United States Patent
McConnell et al.

(10) Patent No.: US 10,555,818 B2
(45) Date of Patent: Feb. 11, 2020

(54) SPINAL FUSION IMPLANT FOR OBLIQUE INSERTION

(71) Applicant: Camber Spine Technologies, LLC, Wayne, PA (US)

(72) Inventors: Jeffrey R. McConnell, Allenton, PA (US); William Duffield, Collegeville, PA (US)

(73) Assignee: Institute For Musculoskeletal Science and Education, Ltd., Wayne, PA (US)

(*) Notice: Subject to any disclaimer, the term of this patent is extended or adjusted under 35 U.S.C. 154(b) by 562 days.

(21) Appl. No.: 15/138,078

(22) Filed: Apr. 25, 2016

(65) Prior Publication Data
US 2016/0310294 A1    Oct. 27, 2016

Related U.S. Application Data

(60) Provisional application No. 62/151,947, filed on Apr. 23, 2015.

(51) Int. Cl.
*A61F 2/44* (2006.01)

(52) U.S. Cl.
CPC .... *A61F 2/4455* (2013.01); *A61F 2002/4475* (2013.01); *A61F 2230/0082* (2013.01)

(58) Field of Classification Search
CPC ................................ A61F 2/44; A61F 2/4455
See application file for complete search history.

(56) References Cited

U.S. PATENT DOCUMENTS

| | | |
|---|---|---|
| 6,302,914 B1 | 10/2001 | Michelson |
| 6,682,564 B1 * | 1/2004 | Duarte ................... A61F 2/447 606/247 |
| RE38,614 E | 10/2004 | Paul |
| 7,125,425 B2 | 10/2006 | Foley |
| 7,291,170 B2 | 11/2007 | Huppert |
| 8,002,837 B2 | 8/2011 | Stream |
| 8,012,208 B2 | 9/2011 | Lechmann |
| 8,216,316 B2 * | 7/2012 | Kirschman ............. A61F 2/447 606/99 |
| 8,246,686 B1 | 8/2012 | Curran |

(Continued)

OTHER PUBLICATIONS

Kim, et al., "Surgical results of the oblique paraspinal approach in upper lumbar disc herniation and thoracolumbar junction", Neurosurgery, 65(1):95-9 (2009).

(Continued)

*Primary Examiner* — David W Bates
(74) *Attorney, Agent, or Firm* — Pabst Patent Group LLP

(57) ABSTRACT

Intervertebral spinal fusion implants for interbody fusion of the anterior column of the spine are described. The implants have a substantially bi-convex or a substantially offset bi-convex shape. The implants are placed through a transforaminal or posterior approach at an oblique insertion angle. The implants have an outermost point on the superior convex surface and an outermost point on the inferior convex surface and four edges of differing heights. The outermost superior and inferior points of the implants are connected with the four edges with convex surfaces of different curvatures. The curvatures of the convex surfaces of the implants are designed to match the curvatures of concave vertebral surfaces when the implants are inserted at an oblique insertion angle.

25 Claims, 13 Drawing Sheets

(56) References Cited

U.S. PATENT DOCUMENTS

| | | | |
|---|---|---|---|
| 8,343,224 B2 | 1/2013 | Lynn | |
| 8,444,696 B2 | 5/2013 | Michelson | |
| 8,480,745 B2 | 7/2013 | Liu | |
| 8,556,976 B2 | 10/2013 | Jacofsky | |
| 8,591,589 B2 | 11/2013 | McCombe | |
| 8,608,804 B2 | 12/2013 | Curran | |
| 8,617,247 B2 | 12/2013 | Lechmann | |
| 8,617,248 B2 | 12/2013 | Ullrich | |
| 8,623,088 B1* | 1/2014 | Tohmeh | A61F 2/4455 623/17.11 |
| 8,679,184 B2 | 3/2014 | Kube, II | |
| 2001/0016745 A1 | 8/2001 | Bullivant | |
| 2004/0186569 A1* | 9/2004 | Berry | A61F 2/44 623/17.11 |
| 2008/0281425 A1* | 11/2008 | Thalgott | A61F 2/4465 623/17.16 |
| 2008/0288076 A1 | 11/2008 | Soo | |
| 2011/0190889 A1* | 8/2011 | Miller | A61F 2/442 623/17.16 |
| 2012/0245640 A1 | 9/2012 | Auerbach | |
| 2012/0277810 A1 | 11/2012 | Siccardi | |
| 2012/0277869 A1 | 11/2012 | Siccardi | |
| 2013/0018466 A1 | 1/2013 | Yu | |
| 2013/0096683 A1* | 4/2013 | Kube, II | A61F 2/442 623/17.16 |
| 2013/0150968 A1* | 6/2013 | Dinville | A61F 2/447 623/17.16 |
| 2014/0277497 A1* | 9/2014 | Bennett | A61F 2/4455 623/17.16 |

OTHER PUBLICATIONS

Lee, et al., "The effect of age on sagittal plane profile of the lumbar spine according to standing, supine, and various sitting positions", J Orthop Surg Res., 9(1):1-10 (2014).

Lin, et al., "Lumbar lordosis: normal adults", J Fomos Med Assoc., 91(3):323-33 (1992).

Medacta, "Oblique and Posterior intervertebral body fusion device", Medacta International, pp. 1-20, https://www.medacta.com/sites/medacta.com/files/.../TO_994412US_rev01.pdf,, retrieved from the internet Jan. 7, 2013.

O'Rahilly, et al., Basic human anatomy, table of contents figure 39-1 and 39-2, Editor Rand Swenson (2009).

Rothbart, Measuring the Lordotic Angle, one page www.rothbartsfoot.es/measuringTheLordosis, retrieved from the internet Jan. 2, 2013.

Signature—Articulating lumbar TLIF spacer, http://www.globusmadical.com/intervertebral-fusion/213-signature, retrieved from the internet Jan. 7, 2013.

Silvestre, et al., "Complications and morbidities of mini-open anterior retroperitoneal lumbar interbody fusion: Oblique lumbar interbody fusion in 179 patients", Asian Spine J., 8(2):89-97 (2012).

Synthes Spine, "Posterior lumbar interbody fusion (PLIF) instruments. Designed for use with the PLIF spacer", Technique guide, pp. 1-24. (1999).

* cited by examiner

SPINAL FUSION IMPLANT FOR OBLIQUE INSERTION

CROSS-REFERENCE TO RELATED APPLICATION

The present application claims priority to U.S. Application No. 62/151,947, filed on Apr. 23, 2015, by Jeffrey R. McConnell and William Duffield, the disclosure of which is incorporated herein by reference in its entirety.

FIELD OF THE INVENTION

This invention relates to implantable devices and methods for use in spinal surgery.

BACKGROUND OF THE INVENTION

The standard treatment for chronic pain related to damaged or displaced discs is lumbar spinal fusion. In preparation for the spinal fusion, a damaged disc is removed entirely. A device, such as an intervertebral cage or implant, can be placed between the vertebrae to restore proper spine alignment and disc height. This also reduces, if not eliminates, neural impingement commonly associated with a damaged or diseased disc.

Minimally invasive methods of performing spinal fusion have gained popularity in recent years due to the many benefits of the procedure, which include diminished dissection of body tissue and lower blood loss during surgery resulting in reduced surgery time, lower post-operative pain and a quicker recovery for patients. Transforaminal lumbar interbody fusion (TLIF) and/or transforaminal posterior interbody fusion (TPLIF) procedures provide unilateral access to a desired target site. The TLIF technique involves approaching the spine in a similar manner as a posterior approach but more from the left or right of the spine through a midline incision in a patient's back. This procedure requires only one incision in the back of a patient.

A challenge in spinal fusion is achieving a proper fit between an implant and the adjacent vertebrae. If an implant is not flush against the concave vertebral plates, then it can loosen and move out of place, resulting in poor fixation.

There remains a need for improved intervertebral fusion implants that fit the geometry of the concave endplates, particularly for an oblique insertion technique.

Therefore, it is an object of the invention to provide improved intervertebral fusion implants.

It is a further object of the invention to provide improved methods for spinal fusion.

It is a further object of the invention to provide kits for intervertebral fusions.

SUMMARY OF THE INVENTION

Intervertebral fusion implants for insertion and positioning at an oblique angle in the intervertebral disc space of two vertebrae, and for matching the concavities of the vertebrae at the oblique insertion angle are described herein, along with methods for using the implants and kits containing the implants. The implants have a superior convex surface, an inferior convex surface, and four vertical edges of differing heights. The curvatures of the convex surfaces define the sagittal and the coronal profiles of the implants. The curvatures of the convex surfaces substantially match the concavities of the adjacent vertebrae, when the implant is inserted into a patient's spine at an oblique insertion angle.

Each of the superior convex surface and the inferior convex surface contains an outermost point. In some embodiments, the shape of the implants is substantially bi-convex. In other embodiments, the shape of the implants is substantially offset bi-convex.

In preferred embodiments, the implants have a central opening for receiving a bone graft material and facilitating bone ingrowth and fusion. In some embodiments, the central opening is divided into two or more compartments by one or more dividers.

Methods of using the bi-convex and offset bi-convex implants are also provided. The implants are inserted at an oblique insertion angle using transforaminal or posterior approach. In preferred embodiments, the oblique insertion angle ranges from 30° to 40° relative to the medial axis of the spine. Bilateral or unilateral insertion methods may be used. The implants may be used alone, or with the supplemental fixation system, to increase or decrease a lordotic angle. Optionally, the implants are used with supplemental fixation systems, such as polyaxial bone screws and rods, to achieve the desired spacing between the vertebral bodies.

Kits providing a plurality of bi-convex and/or offset bi-convex implants with different sizes are also described. A kit may contain implants of different heights, lengths, and/or widths to suit diversities in spinal anatomy. The kits optionally include one or more tools or instruments, such as the supplemental fixation system. Kits may also include osteogenic and/or osteoinductive material(s).

BRIEF DESCRIPTION OF THE DRAWINGS

FIG. 1A is a side view, showing the medial side of the implant, the coronal planes C and A, and the dimensions $a_2$, $a_3$, $a_4$, $b_2$, and $b_3$. FIG. 1B is a top view of the implant showing the coronal planes C and A, and the dimensions $b_1$, $b_2$, $b_3$, $b_4$, $b_{1S}$, $b_{2S}$, $b_{3S}$, and $b_{4S}$. FIG. 1C is a front view showing the posterior side of the implant, the medial axis M, and the dimensions $a_5$, $a_6$, $b_5$, and $b_6$. FIG. 1D is a top view of the implant. FIG. 1E is a side view, showing the medial side of the implant. FIG. 1F is a three-dimensional posterior-medial view of implant, showing the superior, posterior and medial surfaces. FIG. 1G is a three-dimensional posterior-lateral view of the implant, showing superior, lateral and posterior surfaces. FIG. 1H is a three-dimensional anterior-medial view of the implant, showing the superior, anterior, posterior and medial surfaces. FIG. 1I is top view of the implant, showing the oblique insertion angle relative to the medial axis of the spine (MS).

FIG. 2A is a side view, showing the medial side of the implant, the coronal plane C, the anterior coronal plane A, and the dimensions $a_{20}$, $a_{30}$, $a_{40}$ and $b_{20}$ and $b_{30}$. FIG. 2B is a top view of the implant showing the coronal plane C, the anterior coronal plane A, and the dimensions $b_{10}$, $b_{20}$, $b_{30}$, $b_{40}$, $b_{10S}$, $b_{20S}$, $b_{30S}$, and $b_{40S}$. FIG. 2C is a front view showing the posterior side of the implant, the medial axis M, and the dimensions $a_{50}$, $a_{60}$, $b_{50}$, and $b_{60}$. FIG. 2D is a posterior-medial view of the implant showing the superior, anterior, posterior and medial surfaces, the coronal plane C, the anterior coronal plane A, and the dimensions $a_{10}$, $a_{20}$, $a_{30}$, and $a_{40}$. FIG. 2E is a top view of the implant. FIG. 2F is a side view showing the medial side of the implant. FIG. 2G is a three-dimensional posterior-medial view of the implant, showing the superior, posterior and medial surfaces. FIG. 2H is a three-dimensional posterior-lateral view of the implant, showing superior, lateral and posterior surfaces. FIG. 2I is a three-dimensional anterior-medial view of the implant, showing the superior, anterior, posterior and medial surfaces. FIG. 2J is a top view of the implant, showing the oblique insertion angle relative to the medial axis of the spine (MS).

DETAILED DESCRIPTION OF THE INVENTION

I. Intervertebral Fusion Implants

A. Implants

Figure 1A:
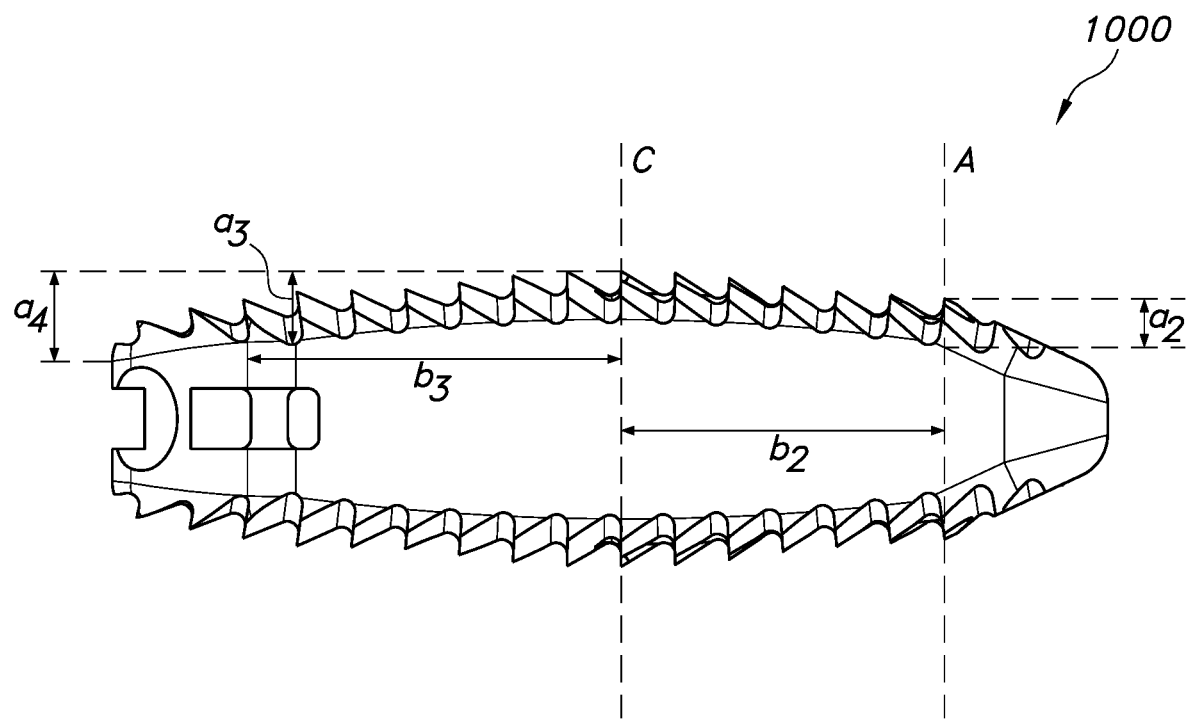
FIGS. 1A-1I depict different views of an exemplary bi-convex intervertebral spinal fusion implant.

The terms "apex of the implant" and "implant apex" are used interchangeably to refer to the outermost point on the superior convex surface. In implants with a bi-convex shape, the apex is positioned about the middle of the implant. In implants with an offset bi-convex shape, the apex is positioned anteriorly or posteriorly relative to the middle of the implant.

The implants have lengths ranging from about 30 mm to about 45 mm, and widths ranging from about 10 mm to about 12 mm. The distance from the apex to the outermost point on the opposite surface is referred to as "the apex height". The apex height is greater than the height of each of the edges. Typically, the apex height for the implants ranges from 5 mm to 25 mm, preferably from 9 mm to 18 mm.

1. Implant Features i. Shape and Heights

The implants are sized and configured to fit between two adjacent vertebrae, and to contact and generally conform to the shape of an inferior endplate of the superior vertebra and a superior endplate of the inferior vertebra.

The implants may be asymmetric along each of the medial (M), coronal (C) and transverse (T) planes of the implant. Alternatively, the implants may be symmetric at least along one of the medial (M), coronal (C) and transverse (T) planes. In a preferred embodiment, the implants are symmetric along the transverse plane of the implant.

As used herein, the term the term "median plane" refers to a vertical plane passing through the center of the implant from the anterior end to the posterior end of the implant and dividing the implant into lateral and medial portions. As used herein, the term "medial axis" refers to a line on the median plane located in the center of the plane and passing from the anterior end to the posterior end of the implant.

As used herein, the term "coronal plane" refers to a vertical plane connecting the lateral side of the implant with the medial side and dividing the implant into anterior and posterior portions. A first coronal plane (C) and a second coronal plane (A) are used to describe the implants. The implants have a first coronal plane (C) that is aligned with the apex of the implant. The second coronal plane (A) is positioned anteriorly, at the anterior lateral vertical edge of the implant. In the bi-convex implant, the coronal plane C is positioned about the middle of the implant (see FIGS. 1A and 1B). In the offset bi-convex implant, the first coronal plane (C) is offset from the middle of the implant and may be located anteriorly or posteriorly relative to the middle of the implant (see FIGS. 2A and 2B). As used herein, the term "coronal axis" refers to a line on the coronal plane located in the center of the plane and passing from the lateral side to the medial side of the implant.

As used herein, the term "transverse plane" refers to a horizontal plane passing from anterior end to the posterior end of the implant and dividing the implant into superior and inferior portions. As used herein, the term "transverse axis" refers to a horizontal line on the transverse plane located in the center of the plane and passing from the anterior end to posterior end of the implant.

As used herein, the term "sagittal plane" refers to a vertical plane passing from the anterior end to posterior end of the implant and dividing the implant into lateral and medial portions.

The outer surfaces of the implants contain a superior convex surface, an inferior convex surface, an anterior vertical surface, a posterior vertical surface, a lateral longitudinal surface, and a medial longitudinal surface. The implants have at least four vertical edges: an anterior lateral vertical edge, an anterior medial vertical edge, a posterior lateral vertical edge and a posterior medial vertical edge. The vertical edges are located where a longitudinal surface meets with a vertical surface. Each of the vertical edges has a superior end and an inferior end, where each superior end terminates at the superior convex surface, and each inferior end terminates at the inferior contact surface. Optionally, the one or more vertical edges are curved.

Each convex surface also has an outermost point. The superior convex surface contains a first outermost point (also referred to as the apex), and the inferior convex surface contains a second outermost point.

The implants contain one or more openings configured to receive bone graft or bone graft substitute. In some embodiments, the opening is divided into one or more sections by one or more dividers. In the bi-convex embodiments, at least a portion of the divider is located at the outermost point of the superior convex surface and the outermost point of the inferior convex surface. The dividers may divide the opening in any manner. In preferred embodiments, a divider is positioned diagonally within an opening of the implants, and divides the opening into substantially equal parts.

In some embodiments, the lateral longitudinal surface and the medial longitudinal surface of the implants are substantially flat. However, these surfaces may have any desired three-dimensional geometry, and are optionally curved surfaces.

a. Shape of Implants

In one embodiment, the shape of the implant is substantially bi-convex.

As used herein, the term "bi-convex" means a cuboid shape, where at least two of the surfaces along the transverse axis of the implant are convex, and wherein the outermost point of the superior convex surface and the outermost point of the inferior convex surface are positioned about the middle of the implant.

In another embodiment, the shape of the implant is substantially offset bi-convex. As used herein, the term "offset bi-convex" means a cuboid shape, wherein at least two of the surfaces along the transverse axis of the implant are convex. The outermost point of the superior convex surface and the outermost point of the inferior convex surface are not positioned in the middle of the implant, rather they are located anteriorly or posteriorly relative to the middle of the implant.

The convex surfaces of the implants generally correspond with a traditional anterior lumbar interbody fusion (ALIF) implant with bi-lateral features cut away from the implants. The cuts are made at an oblique angle to the median plane of the ALIF implant. The oblique angle of the cuts matches the oblique insertion angle. The resulting oblique implant has convex curvatures that match the concavities of the adjacent vertebrae at the oblique insertion angle.

b. Sagittal and Coronal Profiles

As used herein, the term "sagittal profile" refers to the curvature of the implant along a sagittal plane.

As used herein, the term "coronal profile" refers to the curvature of the implant along a coronal plane.

As used herein, the term "apex height" refers to the height of the implant at its apex. It is measured along an imaginary straight line running parallel to the edges and connecting the apex of the implant to the outermost point of the inferior convex surface (or to an imaginary plane containing the outermost point of the inferior convex surface and perpendicular to the imaginary straight line when the outermost point of the inferior convex surface is not vertically aligned with the apex of the implant).

As used herein, the terms "lower-most lateral point" and "lower-most medial point" refer to the lowest points of the superior convex surface that meet the lateral and medial sides, respectively, of an implant along a defined plane. For example, the superior convex surface of an implant has a lower-most lateral point and a lower-most medial point along the coronal plane C of the implant.

As used herein, the terms "upper-most lateral point" and "upper-most medial point" refer to the upper-most points of the inferior convex surface that meet the lateral and medial sides, respectively, along a defined plane. For example, the inferior convex surface of an implant has an upper-most lateral point and an upper-most medial point along the coronal plane C of the implant.

The shape of the sagittal profile is defined by connecting the outermost point of the superior convex surface with the superior ends of the four edges via convexly curved surfaces, and similarly connecting the outermost point of the inferior convex surface with the inferior ends of the four edges via convexly curved surfaces.

The shape of the coronal profile is defined by connecting the outermost point of the superior convex surface with the lower-most lateral point and lower-most medial point along the coronal axis C via convexly curved surfaces along the coronal plane of the implant, and similarly connecting the outermost point of the inferior convex surface with the upper-most lateral point and upper-most medial point via convexly curved surfaces along the coronal plane C of the implant.

(a) Curvature

The curvature of the superior and inferior convex surfaces may be represented by superior curved lines and inferior curved lines, respectively (the terms "curved line" and "arc" can be used interchangeable). In preferred embodiments, each of the superior curved lines has a different curvature, and the inferior convex surface contains the same curvature as the superior convex surface. The curvature may be represented by the eccentricity of the superior curved lines and inferior curved lines, which can be calculated using Equation 1 below:

$$E = \frac{\sqrt{b^2 - a^2}}{b} \quad \text{(Eq. 1)}$$

wherein

E is eccentricity of a curved line;

a is the difference between the apex height and the height of the edge (sagittal profile), or the difference in height between the outermost point and the lower-most lateral point or the lower-most medial point (coronal profile); and b is the length of a straight line from an edge to the coronal plane passing through the outermost point, and connecting with the coronal plane at a right angle (sagittal profile), or the length of a straight line from the lateral point or medial point to the median plane, and connecting with the median plane at a right angle (coronal profile).

In some embodiments, b is the length of a straight line running from the edge to the first or second outermost point.

The values for a and b are measured along defined lines, as indicated in FIGS. 1A-1C, 1G and 2A-2D.

In general, the curvatures of the superior convex surface and inferior convex surface of the bi-convex implants are defined by the dimensions $a_1$, $a_2$, $a_3$, $a_4$, $a_5$, and $a_6$, and $b_1$, $b_2$, $b_3$, $b_4$, $b_{1S}$, $b_{2S}$, $b_{3S}$, $b_{4S}$, $b_5$, and $b_6$, as described above and as shown in FIGS. 1A-1C, and 1G. In general, the curvatures of the offset bi-convex implants are defined by the dimensions $a_{10}$, $a_{20}$, $a_{30}$, $a_{40}$, $a_{50}$, $a_{60}$, and $b_{10}$, $b_{20}$, $b_{30}$, $b_{40}$, $b_{10S}$, $b_{20S}$, $b_{30S}$, $b_{40S}$, $b_{50}$ and $b_{60}$, as shown in FIGS. 2A-2D.

In preferred embodiments, each of the curved lines has its own curvature represented by dimensions a and b. For example, in one embodiment, the superior convex surface of a bi-convex implant may have different values for a, designated as $a_1$, $a_2$, $a_3$ and $a_4$, and different values for b, designated as $b_1$, $b_2$, $b_3$, $b_4$, $b_{1S}$, $b_{2S}$, $b_{3S}$, and $b_{4S}$. Each of the $a_1$, $a_2$, $a_3$ and $a_4$ values may range from 0.03 mm to 0.15 mm, and each of the $b_1$, $b_2$, $b_3$, $b_4$, $b_{1S}$, $b_{2S}$, $b_{3S}$, and $b_{4S}$ may range from 11.5 mm to 21 mm, along the sagittal plane. In some embodiments, the dimensions $b_1$, $b_2$, $b_3$, $b_4$, $b_{1S}$, $b_{2S}$, $b_{3S}$, and $b_{4S}$ have equal values. In other embodiments, the dimensions $b_1$, $b_2$, $b_3$, $b_4$, $b_{1S}$, $b_{2S}$, $b_{3S}$, and $b_{4S}$ have different values.

The same implant may have two other values for a, $a_5$ and $a_6$, and two other values for b, $b_5$ and $b_6$, along the coronal plane (C). The $a_5$ and $a_6$ values may each range from 0.5 mm to 0.88 mm, and each of the $b_5$ and $b_6$ values may range from 5 mm to 6 mm. In some embodiments, the dimensions $b_5$ and $b_6$ have equal values. The inferior convex surface has the same or similar values for a and b.

In another embodiment, the superior convex surface of an offset bi-convex implant may have different values for a, designated as $a_{10}$, $a_{20}$, $a_{30}$ and $a_{40}$, and different values for b, designated as $b_{10}$, $b_{20}$, $b_{30}$, $b_{40}$, $b_{10S}$, $b_{10S}$, $b_{30S}$, and $b_{40S}$. Each of the $a_{10}$, $a_{20}$, $a_{30}$ and $a_{40}$ values may range from 1.6 mm to 4.2 mm, and each of the $b_{10}$, $b_{20}$, $b_{30}$, $b_{40}$, $b_{10S}$, $b_{20S}$, $b_{30S}$, and $b_{40S}$ may range from 7.2 mm to 28.3 mm, along the sagittal plane. In some embodiments, the dimensions $b_{10}$, $b_{20}$, $b_{30}$, $b_{40}$, $b_{10S}$, $b_{20S}$, $b_{30S}$, and $b_{40S}$ have equal values. In other embodiments, the dimensions $b_{10}$, $b_{20}$, $b_{30}$, $b_{40}$, $b_{10S}$, $b_{20S}$, $b_{30S}$, and $b_{40S}$ have different values.

The same implant may have two other values for a, $a_{50}$ and $a_{60}$, and two other values for b, $b_{50}$ and $b_{60}$, along the coronal plane (C). The $a_{50}$ and $a_{60}$ values may each range from 0.5 mm to 1.1 mm, and each of the $b_{50}$ and $b_{60}$ values may range from 5 mm to 6 mm. In some embodiments, the dimensions $b_{50}$ and $b_{60}$ have equal values.

Figure 2A:
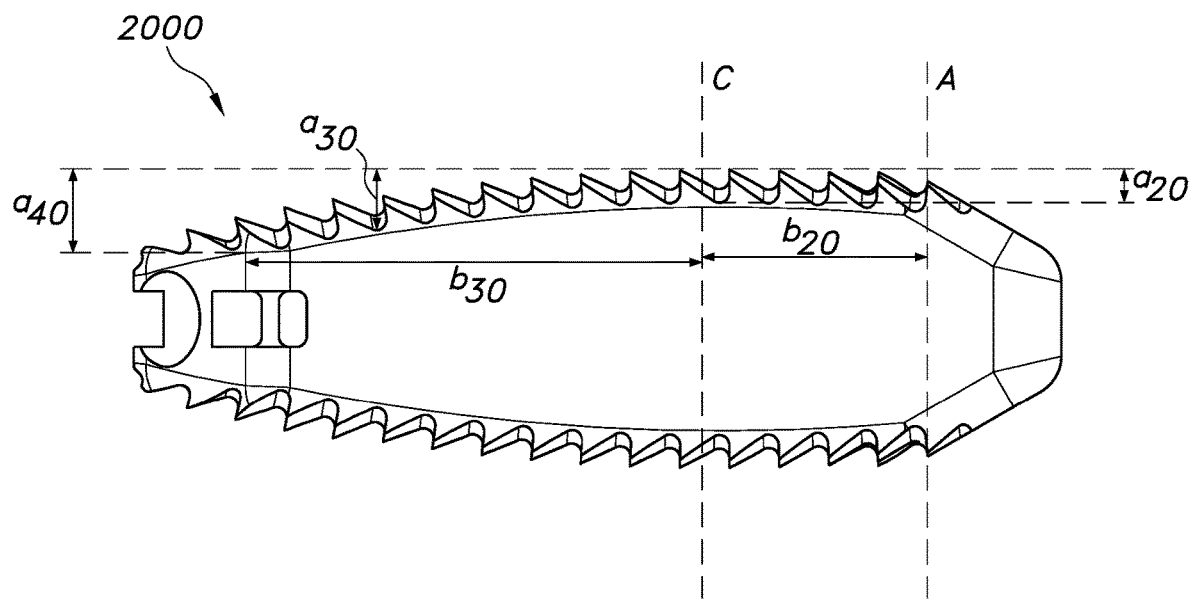
FIGS. 2A-2J depict different views of an exemplary offset bi-convex intervertebral spinal fusion implant.

In a specific example, the curvature of the curved line (arc) connecting the apex of the superior convex surface with the anterior medial vertical edge may be calculated using the Equation 1 above, where a is $a_2$ and b is $b_2$, as shown in FIG. 1A.

These curved surfaces of the implants are configured to match the concave surfaces of the endplates of the adjacent vertebrae when the implants are inserted into a patient's spine, between two vertebrae, from a posterior oblique angle.

c. Heights of Implant Vertical Edges

Various heights are acceptable for the implants. The implant has a suitable height to fit in the intervertebral disc space.

As used herein, the term "implant heights" refers to heights of different elements in the implants, typically the vertical edges, and/or the overall height of the implant, i.e. the apex height. The heights described herein include the bone engagement members on the surfaces of the implants.

The term "overall implant height" as generally used herein refers to height of the implant at its highest point, i.e., the apex height. Typically, the overall implant height ranges from 5 mm to 25 mm. In preferred embodiments, the overall implant height ranges from 9 mm to 18 mm.

The four vertical edges of the implants may differ in height from one another. In a preferred embodiment, the anterior lateral vertical edge is the highest; the anterior medial vertical edge is shorter than the anterior lateral vertical edge; the posterior lateral vertical edge is shorter than anterior medial vertical edge; and the posterior medial vertical edge is shorter than the posterior lateral vertical edge. Generally, the posterior vertical surface of the implant is shorter in height than the anterior vertical surface.

ii. Lengths and Widths

Various lengths (L) and/or widths (W) are acceptable for the implants. The implant has a suitable length and width to fit in the intervertebral disc space.

Typically, the implant length ranges from 30 mm to 45 mm. Preferably, the implant length is 34 mm, 39 mm, or 41 mm.

Typically, the implant width ranges from 5 mm to 18 mm, optionally the width ranges from 5 mm to 15 mm, 6 mm to 18 mm, or 9 mm to 18 mm. In preferred embodiments, the implant width ranges from 10 mm to 12 mm.

iii. Insertion Angles

The implants are designed for a posterior transforaminal insertion technique. Typically, the implants are inserted posteriorly at an acute, oblique, angle relative to the medial axis (MS) of the spine. Typically, the insertion angle ranges from 30° to 40°, preferably about 35°, relative to the MS of the spine. This insertion angle is depicted in FIGS. 1I, 2J, 3, 5 and 6.

iv. Surfaces

The superior convex surface and the inferior convex surfaces of the implants typically contain one or more bone engagement members. The engagement members may cover a surface, or cover only a portion of a surface. The bone engagement members may be present on one or more surfaces. The engagement members increase the frictional resistance between the surfaces of the implants and the adjacent vertebral bodies compared to the same surface without the features or texture, thereby increasing the stability of the implant within the patient's spine. Suitable engagement members include, but are not limited to, ridges, grooves, dimples, nodules, bumps, raised portions or patterns, or any combination thereof.

An engagement member may be a textured surface. A textured surface can have any surface roughness. Surface roughness refers to deviations in the direction of the normal vector of a real surface from its ideal form. In some embodiments, a textured surface has a surface roughness from 1 micron to 2 mm, from 0.01 mm to 1.5 mm, from 0.1 mm to 1.5 mm, or from 0.25 mm to 1.0 mm.

2. Implant Materials

In some embodiments, the implants may be formed from a thermosetting polymer. Biologically stable thermosetting polymers include, but are not limited to, polyethylene, polymethylmethacrylate, polyurethane, polysulfone, polyetherimide, polyimide, ultra-high molecular weight polyethylene (UHMWPE), cross-linked UHMWPE and members of the polyaryletherketone (PAEK) family, including polyetheretherketone (PEEK), carbon-reinforced PEEK, and polyetherketoneketone (PEKK). Preferred thermosetting polymers include, but are not limited to, polyetherketoneketone (PEKK) and polyetheretherketone (PEEK). PEEK is particularly suitable because its modulus of elasticity closely matches that of bone. However, PEEK is also a hydrophobic material and bacteria tend to adhere to these types of surfaces.

In some embodiments, a thermoplastic resin material, such as PEEK, is modified to increase surface hydrophobicity and/or is coated with an antibacterial agent.

In some embodiments, the implants may contain a metal, such as titanium, stainless steel, tantalum, cobalt-chrome, or any other biocompatible metal, or a combination thereof. Optionally, the metal is coated with a thermosetting polymer.

B. Markers

The implants are typically formed from a radiolucent material. To help with non-invasive visualization of the implants, the implants optionally contain imaging markers, which include, but are not limited to markers for radiographic, ultrasonic, magnetic resonance and/or computed tomography imaging. The imaging markers may be positioned at any location in the implant that does not interfere with the implant's performance. In preferred embodiments, one or more markers are positioned at the anterior and/or posterior ends of the implant. In one embodiment, one or more markers may be positioned at the anterior medial vertical edge of the implant, one or more markers may be positioned at the posterior lateral vertical edge of the implant, and one or more markers may be positioned in the oblique divider, if a divider is present.

C. Bone Graft Materials

In preferred embodiments, the opening contains an osteogenic or osteoinductive material. Any suitable osteogenic or osteoinductive material or composition is contemplated for placement within the opening. Such materials include, but are not limited to, autograft, allograft, xenograft, demineralized bone, synthetic and natural bone graft substitutes, such as bioceramics and polymers, and osteoinductive factors. Where bony material is placed within the opening, the material can be pre-packed into the opening before the implant is implanted. A separate carrier to hold the materials within the cavities of the implants can also be used. These carriers can include collagen-based carriers, bioceramic materials, such as BIOGLASS®, hydroxyapatite and calcium phosphate compositions.

The carrier can be in the form of a sponge, a block, folded sheet, putty, paste, graft material or another suitable form.

The osteogenic compositions for placement in the opening of the bi-convex and the offset bi-convex implants may include an effective amount of one or more active agents, such as bone morphogenetic proteins, transforming growth factor beta 1, insulin-like growth factor 1, platelet-derived growth factor, fibroblast growth factor, LIM mineralization protein (LMP), and combinations thereof. Optionally, other therapeutic or infection resistant agents may be in the opening, preferably confined within a suitable carrier material. Active agents can be any compound or compositions that have a biological effect. Preferred active agents are those that will complement and/or enhance the use and function of the implants.

D. Insertion Tools

The posterior surface of the implants may have one or more instrument regions for receiving an insertion instrument. Suitable instruments include, but are not limited to posterior or oblique insertion tools, and posterior or oblique implantation tools. The tools have features for securing and stabilizing the implants, such as outer threads and lateral protrusions. The instrument regions of the implants are configured to mate with the securing and stabilization features of the insertion instruments.

In some embodiments, the instrument regions include a cavity with inner threads. The inner threads may be designed to mate with corresponding outer threads on an insertion tool. In some embodiments, the instrument regions of implants include indented cuts on one or more of the edges. In some embodiments, the indented cuts are present at the posterior edges. The indented cuts may be configured to receive lateral protrusions of an insertion tool.

II. Kits

A. Implants

Variations in implant heights, length (L) and/or implant width (W) are needed to accommodate the diversity in patients' spinal anatomy. In preferred embodiments, kits are configured to provide a plurality of implants of various sizes. In some embodiments, the plurality of implants includes two to five implants of different sizes, in other embodiments the plurality of implants may include five to ten or more differently sized implants.

In some embodiments, the kits are configured to provide tools necessary for sizing the intervertebral disc space and selecting an implant of the right size and fit. These sizing tools include trial spacers of one or more sizes to facilitate selection of an appropriately sized implant. The trial spacer is typically inserted into the intervertebral space and removed therefrom prior to insertion of the implant.

B. Supplemental Fixation System

The implants are configured to be used with a supplemental fixation system for use in lumbar spine surgeries. Optionally, the kit includes at least one suitable supplemental fixation system. Suitable supplemental fixation systems include, but are not limited to, polyaxial bone screws and/or pedicle screws with rods. For example, a kit may contain a bi-lateral system with a pedicle screw and rod assembly for fixation of two or more vertebra, including the vertebra positioned immediately above and below the implants.

C. Graft Material

In some embodiments, the kits include a synthetic bone graft substitute and/or a natural bone graft material, such as bioceramics or polymers, and/or osteoinductive factors.

The kits may also include separate carriers to contain the materials within the cavities of the implants.

D. Instructions for Use

In preferred embodiments, the kits include instructions for use.

III. Methods of Use

The implants may be used in intervertebral body fusion procedures in skeletally mature patients with degenerative disc disease (DDD) of the lumbar spine at one or two contiguous levels from L2-S1. DDD refers to discogenic pain with degeneration of the disc confirmed by history and radiographic studies. DDD patients may also have up to Grade I spondylolisthesis or retrolisthesis at the involved level(s). In preferred embodiments, the implants described herein are used with an autologous bone graft, or bone graft substitute, and implanted via an open transforaminal or posterior approach. In preferred embodiments, the implants are used with supplemental fixation systems.

Following implantation, the implant is firmly seated with a secure fit between the endplates of the adjacent vertebrae when the segment is fully distracted. Preferably, the tallest possible implant is used to maximize segmental stability.

A. Preparation of Discs and Endplates

In preferred embodiments, the discs are prepared by the removal of the disc until only the anterior and lateral annuli remain. The use the scrapers, rasps, curettes, etc., may assist in the removal of the nucleus pulpous and the superficial layer of the cartilaginous endplates. The superficial layers of the entire cartilaginous endplates may be removed to expose bleeding bone.

Adequate preparation of the endplates facilitates vascular supply to the implant, optionally with bone graft. Excessive cleaning, however, may weaken the endplates due to removal of bone underlying the cartilaginous layers. Removing the entire endplate may result in subsidence and loss of segmental stability.

B. Distraction

Distraction blades suitable for use include distractors available for posterior lumbar interbody fusion (PLIF) surgeries. Other distractors include distractors for minimally invasive spinal procedures that are used to distract the disc space. Commercially available suppliers of distractors include TeDan Surgical Innovations and Synthesis Holding AG.

The distractor blades are typically inserted into the disc space until the blades rest in the vertebral body. Fluoroscopy may be used to confirm that the distractor blades are parallel to the endplates. Distractor blades are angled cranially when properly placed. The disc space is then distracted.

C. Determination of Implant Size

Figure 3:
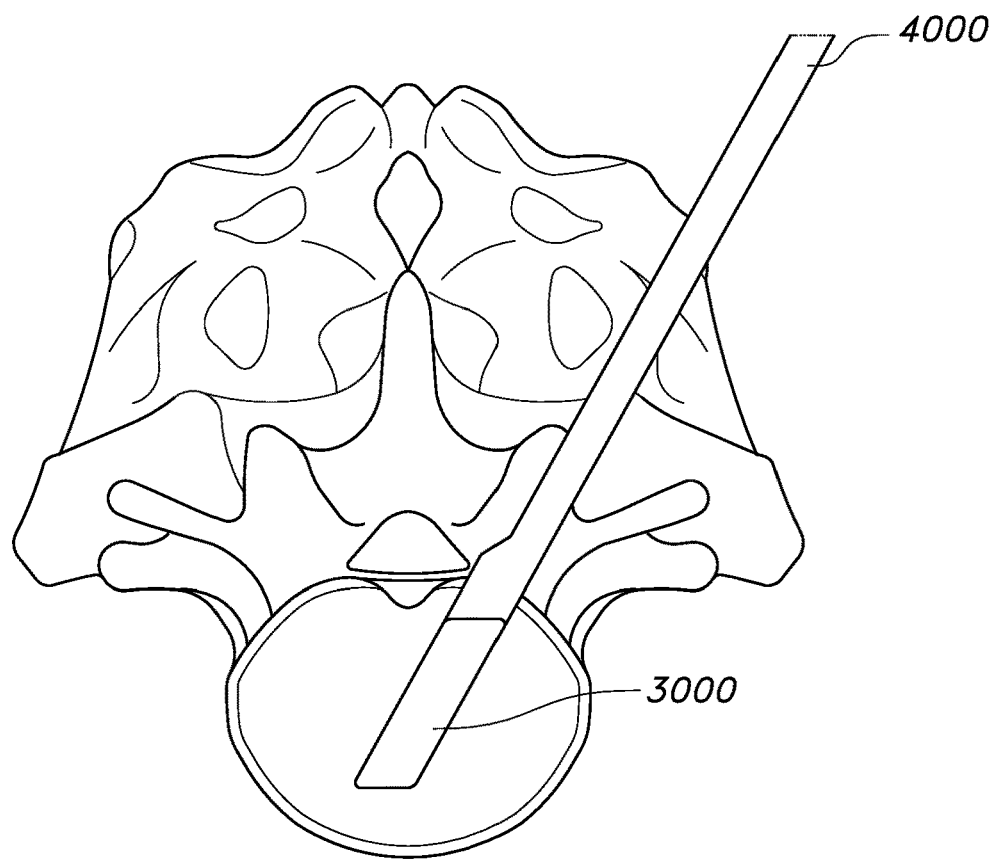
FIG. 3 depicts a top view of a spinal vertebra with a trial spacer attached to an insertion handle and inserted posteriorly at an oblique insertion angle.

A trial spacer 3000 may be inserted into the intervertebral space to select a correctly fitting implant, as shown in FIG. 3.

After distraction, an appropriate sized trial spacer may be connected to the insertion handle 4000. The trial spacer is inserted into the contralateral disc space with gentle impaction. Fluoroscopy and tactile judgment may assist in confirming the fit of the trial spacer. If the trial spacer appears too loose or too tight, an alternative lordotic profile, and/or an alternative height, and/or an alternative length, and/or alternative width implant should be tried until a secure fit is achieved. An implant corresponding to the correct trial spacer is then selected. The trial spacer assembly is removed. A slap hammer may be used to assist with removal.

D. Packing Autologous Bone Graft

Optionally, the implant may be prefilled with a bone graft or bone graft substitute. The autologous bone graft, or bone graft substitute, may be packed within the opening(s) of the implant using a graft loading block.

Alternatively, bone graft, bone graft substitute, or one or more precursor materials for forming a bone graft substitute, may be delivered to the opening(s) after insertion of the implant in a patient.

E. Insertion of the Implant

Figure 4:
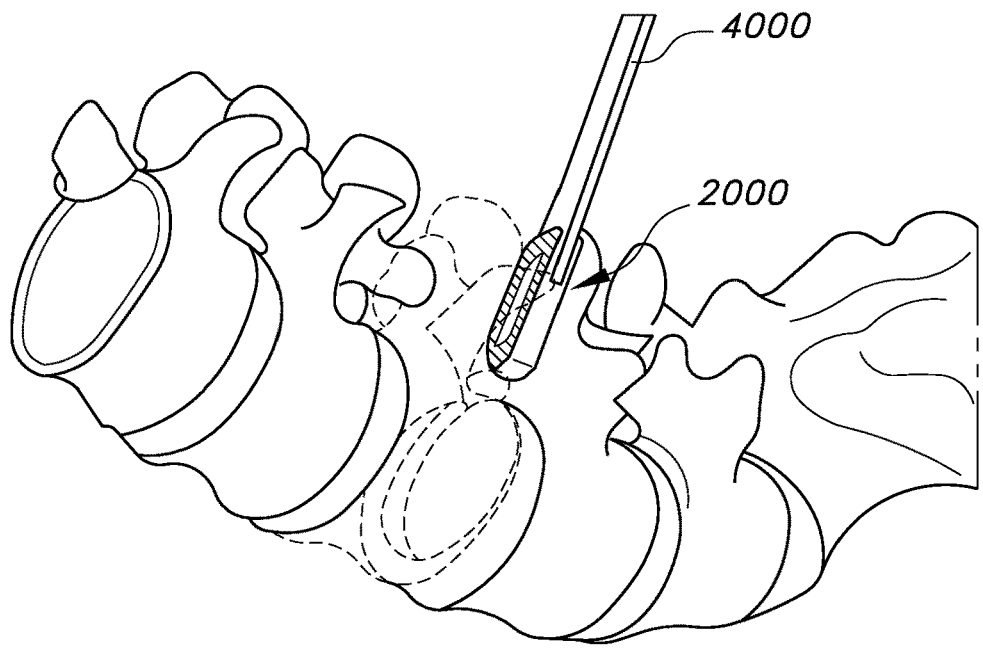
FIG. 4 depicts a three-dimensional anterior-lateral view of a spine and an implant attached to an insertion tool, which is approaching the spine posteriorly.
Figure 5:
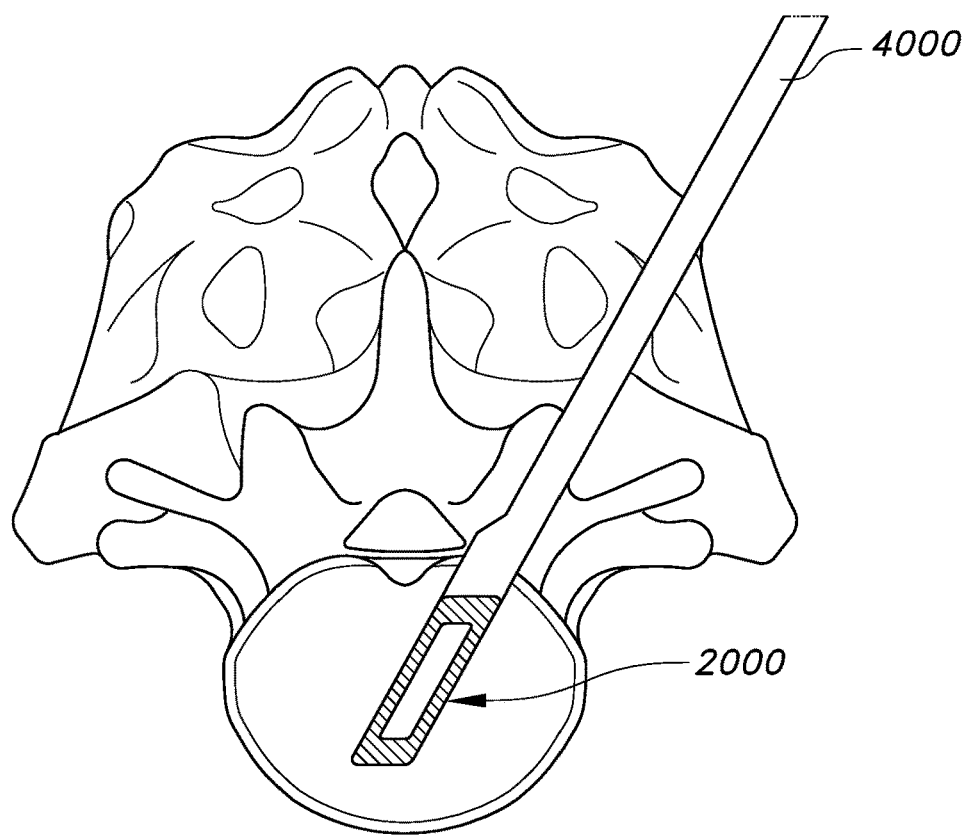
FIG. 5 is a top view of a spinal vertebra with an implant attached to an insertion tool, which is inserted posteriorly at an oblique insertion angle.
Figure 6:
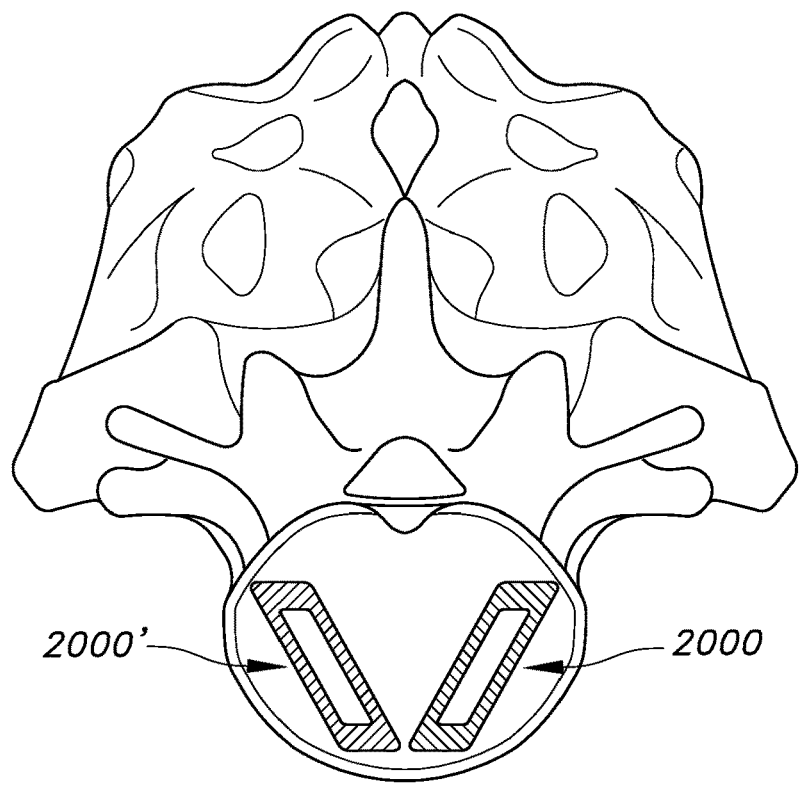
FIG. 6 is a top view of a spinal vertebra with two implants positioned bilaterally, when inserted posteriorly at an oblique insertion angle.

Following preparation of the disc space, an appropriate sized implant is attached to an insertion tool via its tool region. For example, the implant may be threaded onto a threaded rod of an insertion handle, as shown in FIG. 4. Any suitable implant may be used. As shown in FIG. 4, the implant may be an offset bi-convex implant 2000. The implant 2000 and the insertion tool 4000 are then oriented at an oblique insertion angle and introduced into the contralateral disc space, such as indicated in FIGS. 5 and 6. The implant should be aligned with a disc space in a specific orientation, such that the medial longitudinal surface of the implant is placed in the medial direction. Following insertion, the implant should not be rotated. Rotation could result in the wrong orientation of the implant or the implant could be stressed improperly.

Optionally, light impaction may be used to properly seat the implant in the disc space. Once the implant is in the desired position, the insertion rod is unthreaded or otherwise released from the implant.

If a bi-lateral approach is used, prior to placement of a second implant 2000', autologous bone graft is preferably placed in the anterior and medial aspect of the vertebral disc space.

A second implant of the same profile, length, width, and height is inserted into the available disc space as described above with respect to the first implant. The second implant 2000' is oriented medially. The implant is designed for a symmetrical fit in the intervertebral disc space when used in a bi-lateral approach, as depicted in FIG. 6.

Optionally, light impaction is used to properly seat the second implant in the disc space.

Typically the implant is recessed about 2 mm-4 mm beyond the posterior rim of the vertebral body. To achieve insertion with the 2 mm-4 mm recess, the implant may be subtly tamped into the disc space. Preferably, the location of the implant is confirmed via imaging, such as x-ray. These steps are repeated until the implant is about 2-4 mm recessed in the disc space.

F. Supplemental Fixation

The implants described herein may be used with a supplemental fixation system. Supplemental fixation systems with one or more polyaxial screws and one or more rods (e.g. to form lateral connections between the screws) may be used. Supplemental fixation systems may contain one or more bone screws, or one or more pedicle screws, optionally with one or more rods. Following implantation and supplemental fixation, the lordotic angle may be increased or decreased with the help of the supplemental fixation system. For example, an increase in the lordotic angle can be achieved when the polyaxial screws on the same rod securing the superior and inferior vertebra around the implant are moved closer to each other. Similarly, a decrease in the lordotic angle can be achieved when these screws are moved away from each other. The lordotic angle may be measured by any suitable means adopted by a treating physician. For example, the lordotic angle between the upper plate of the first lumbar and first sacral vertebral bodies, may be measured as described in Lee et al., *J. Orthopaedic Surgery and Research*, 9:11 (2014).

G. Removal Technique

In the cases where removal of the implant or revision surgery is required, a surgeon typically studies one or more images, such as radiographic images, noting relevant information, such as: implant position, which can affect optimum surgical approach; the presence of any scar tissue, which can make exposure more challenging than in the un-operated spine; and the position of supplemental fixation.

An implant removal tool and/or an implant insertion tool may be used to engage the implant and remove it. A slap hammer can be utilized to aid in removal.

IV. Exemplary Embodiments

Those skilled in the art will recognize, or be able to ascertain using no more than routine experimentation, many equivalents to the specific embodiments of the implants described herein. Such equivalents are intended to be encompassed by the following exemplary embodiments.

The elements used to describe the bi-convex and offset bi-convex implant shapes, and their corresponding numbers, are presented in Tables 1 and 2, respectively.

TABLE 1

The bi-convex implant elements used to describe the implant.

| Elements used to describe the bi-convex implant | Element number |
| --- | --- |
| superior convex surface | 1100 |
| outermost point of the superior convex surface | 1101 |
| lower-most lateral point | 1120 |
| curved line connecting 1101 to 1500 | 1122 |
| curved line connecting 1101 to 1560 | 1124 |
| curved line connecting 1101 to 1120 | 1126 |
| curved line connecting 1101 to 1140 | 1128 |
| superior horizontal line | 1130 |
| lower-most medial point | 1140 |
| curved line connecting 1101 to 1422 | 1142 |
| curved line connecting 1101 to 1540 | 1144 |
| bone engagement members | 1160 |
| anterior marker | 1170 |
| posterior marker | 1180 |
| middle marker | 1190 |
| inferior convex surface | 1200 |
| outermost point of the inferior convex surface | 1201 |
| upper-most lateral point | 1220 |
| curved line connecting 1201 to 1500 | 1222* |
| curved line connecting 1201 to 1560 | 1224* |
| curved line connecting 1201 to 1220 | 1226* |
| curved line connecting 1201 to 1240 | 1228* |
| upper-most medial point | 1240 |
| curved line connecting 1201 to 1422 | 1242* |
| curved line connecting 1201 to 1540 | 1244* |
| inferior horizontal line | 1260* |
| anterior vertical surface | 1300 |
| posterior vertical surface | 1320 |
| instrument portion | 1322 |
| inner threads | 1324 |
| indented cut | 1326 |
| indented cut | 1328 |
| lateral longitudinal surface | 1400 |
| medial longitudinal surface | 1420 |
| vertical anterior medial edge | 1422 |
| anterior lateral vertical edge | 1500 |
| anterior medial vertical tip | 1520 |
| posterior medial vertical edge | 1540 |
| posterior lateral vertical edge | 1560 |
| central opening | 1600 |
| oblique divider | 1620 |
| anterior chamber | 1640 |
| posterior chamber | 1660 |
| superior oblique surface | 1700 |
| inferior oblique surface | 1720 |

*element not shown in the Figures

TABLE 2

The offset bi-convex implant elements used to describe the implants.

| Elements used to describe the offset bi-convex implant | Element number |
|---|---|
| superior convex surface | 2100 |
| outermost point of the superior convex surface | 2101 |
| lower-most lateral point | 2120 |
| curved line connecting 2101 to 2500 | 2122 |
| curved line connecting 2101 to 2560 | 2124 |
| curved line connecting 2101 to 2120 | 2126 |
| curved line connecting 2101 to 2140 | 2128 |
| superior horizontal line | 2130 |
| lower-most medial point | 2140 |
| curved line connecting 2101 to 2422 | 2142 |
| curved line connecting 2101 to 2540 | 2144 |
| bone engagement members | 2160 |
| anterior marker | 2170 |
| posterior marker | 2180 |
| inferior convex surface | 2200 |
| outermost point of the inferior convex surface | 2201 |
| upper-most lateral point | 2220 |
| curved line connecting 2201 to 2500 | 2222* |
| curved line connecting 2201 to 2560 | 2224* |
| curved line connecting 2201 to 2220 | 2226 |
| curved line connecting 2201 to 2240 | 2228 |
| upper-most medial point | 2240 |
| curved line connecting 2201 to 2422 | 2242* |
| curved line connecting 2201 to 2540 | 2244* |
| inferior horizontal line | 2260 |
| anterior vertical surface | 2300 |
| posterior vertical surface | 2320 |
| instrument portion | 2322 |
| inner threads | 2324 |
| indented cut | 2326 |
| indented cut | 2328 |
| lateral longitudinal surface | 2400 |
| medial longitudinal surface | 2420 |
| vertical anterior medial edge | 2422 |
| anterior lateral vertical edge | 2500 |
| anterior medial vertical tip | 2520 |
| posterior medial vertical edge | 2540 |
| posterior lateral vertical edge | 2560 |
| central opening | 2600* |
| superior oblique surface | 2700 |
| inferior oblique surface | 2720 |

*element not shown in the Figures

A. Bi-Convex Implant

1. Heights and Shape

Figure 1B:
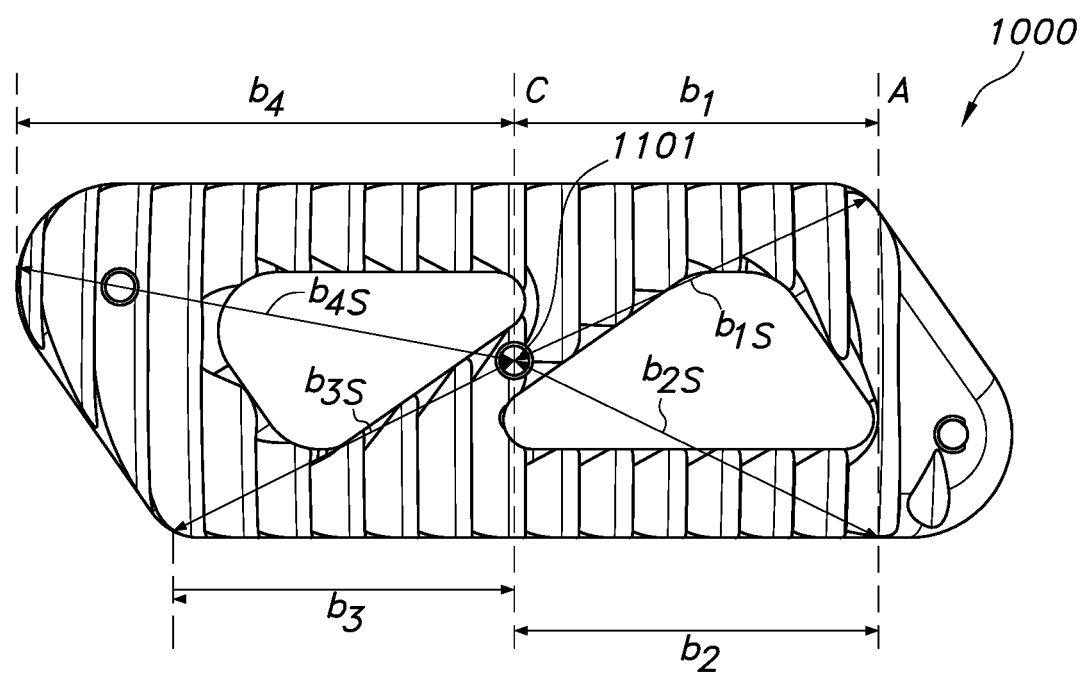
Figure 1C:
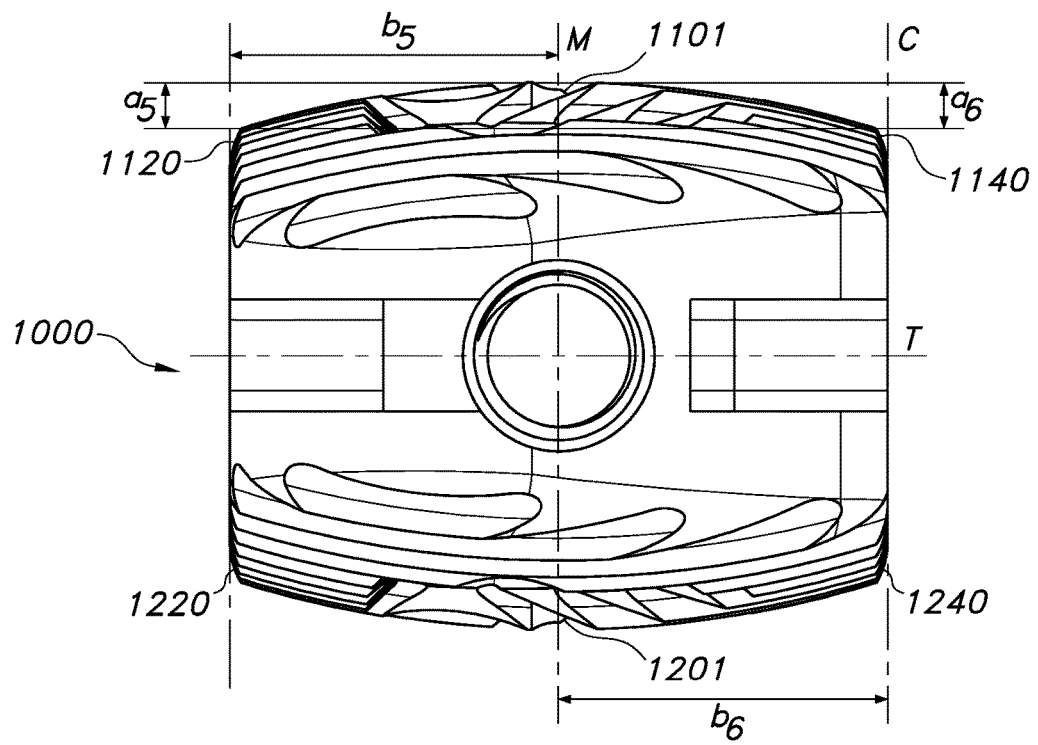
Figure 1D:
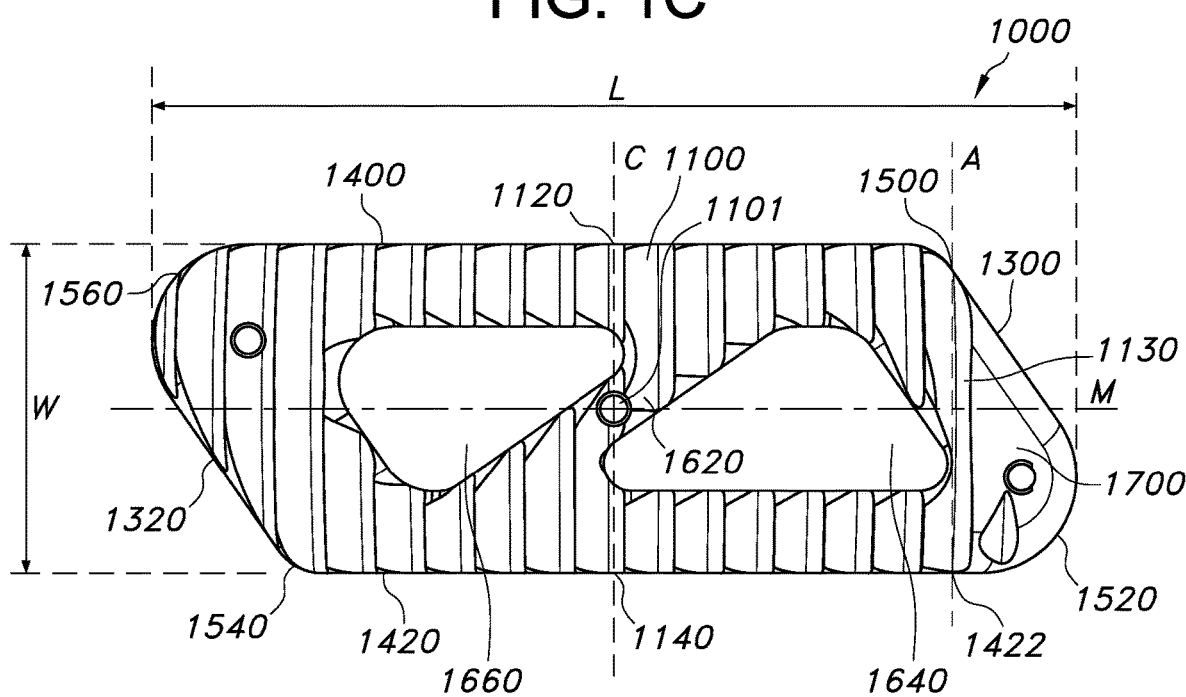

In one embodiment, the shape of the implant is substantially bi-convex. The implants are asymmetric along the medial M and coronal C planes, but symmetric along the transverse T plane, as shown in FIGS. 1C and 1D.

FIGS. 1A-1I depict the general shape of a typical bi-convex implant.

The bi-convex implant 1000 is formed of a superior convex surface 1100, an inferior convex surface 1200, an anterior vertical surface 1300, a posterior vertical surface 1320, a lateral longitudinal surface 1400, a medial longitudinal surface 1420, an oblique divider 1620 dividing a central opening 1600 into substantially equal parts, such as anterior chamber 1640 and posterior chamber 1660.

The anterior vertical surface 1300 meets with the lateral longitudinal surface 1400 and the medial longitudinal surface 1420 forming the anterior lateral vertical edge 1500 and anterior medial vertical tip 1520. Similarly, the posterior vertical surface 1320 meets with lateral longitudinal surface 1400 and the medial longitudinal surface 1420 forming the posterior lateral vertical edge 1560 and posterior medial vertical edge 1540. Each of the vertical edges 1500, 1422, 1540, and 1560 has a superior end and an inferior end that contact the superior convex surface 1100 and the inferior convex surface 1200, respectively. In preferred embodiments, the edges 1500, 1540, and 1560 are curved. As shown on the figures, the anterior lateral vertical edge 1500, anterior medial vertical tip 1520, posterior medial vertical edge 1540, and posterior lateral vertical edge 1560 generally correspond with the ends of the lateral and medial longitudinal surfaces, while the vertical anterior medial edge 1422 is an imaginary line located along the medial longitudinal surface 1420 towards the anterior end.

At the anterior end of the implant, the anterior lateral vertical edge 1500 is connected with the medial longitudinal surface 1420 along an anterior coronal plane A perpendicular to the medial longitudinal surface 1420. The anterior coronal plane A intersects the medial longitudinal surface 1420 along a vertical anterior medial edge 1422. The vertical anterior medial edge 1422 has a superior end contacting the superior convex surface 1100 and an inferior end contacting the inferior convex surface 1200. The anterior coronal plane A intersects the superior convex surface 1100 along a superior horizontal line 1130, and the inferior convex surface 1200 along an inferior horizontal line 1260 (not shown). From the superior horizontal line 1130, the superior convex surface 1100 tapers downwards and forms the superior oblique surface 1700. From the inferior horizontal line 1260 (not shown), the inferior convex surface 1200 tapers upwards and forms the inferior oblique surface 1720.

i. Heights of Implant Elements

Figure 1E:
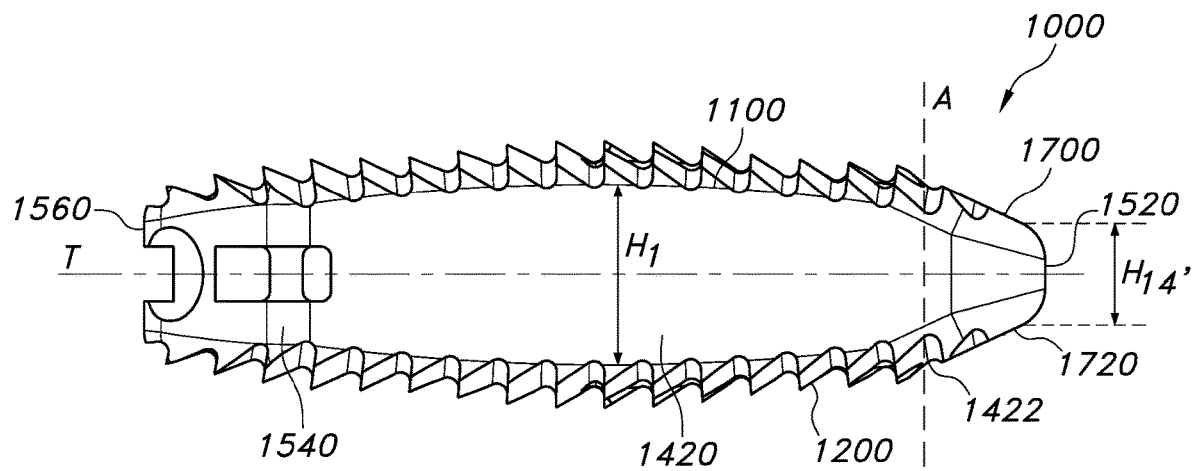
Figure 1F:
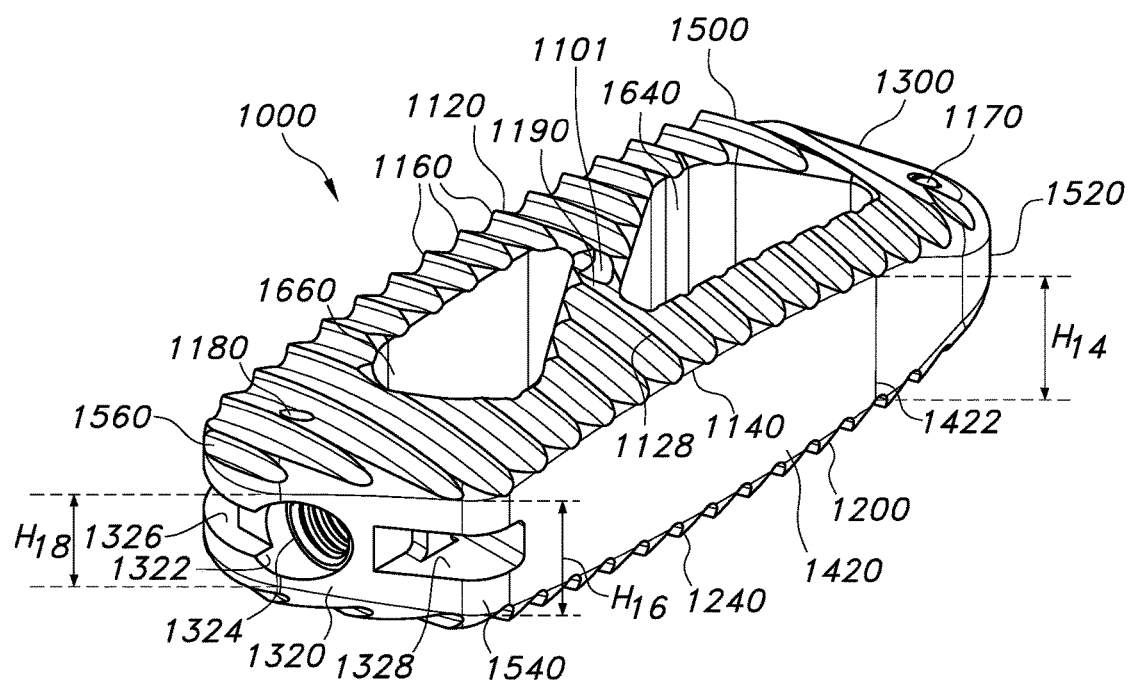
Figure 1G:
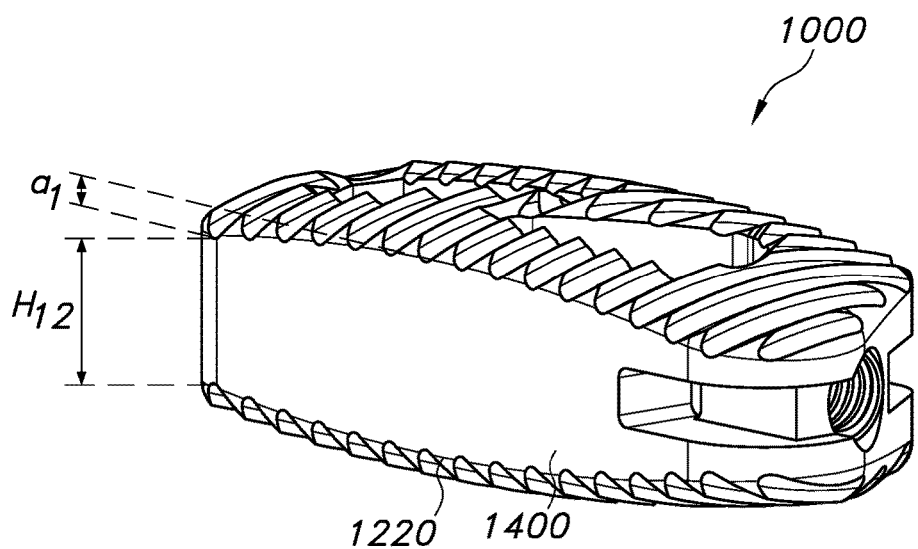
Figure 1H:
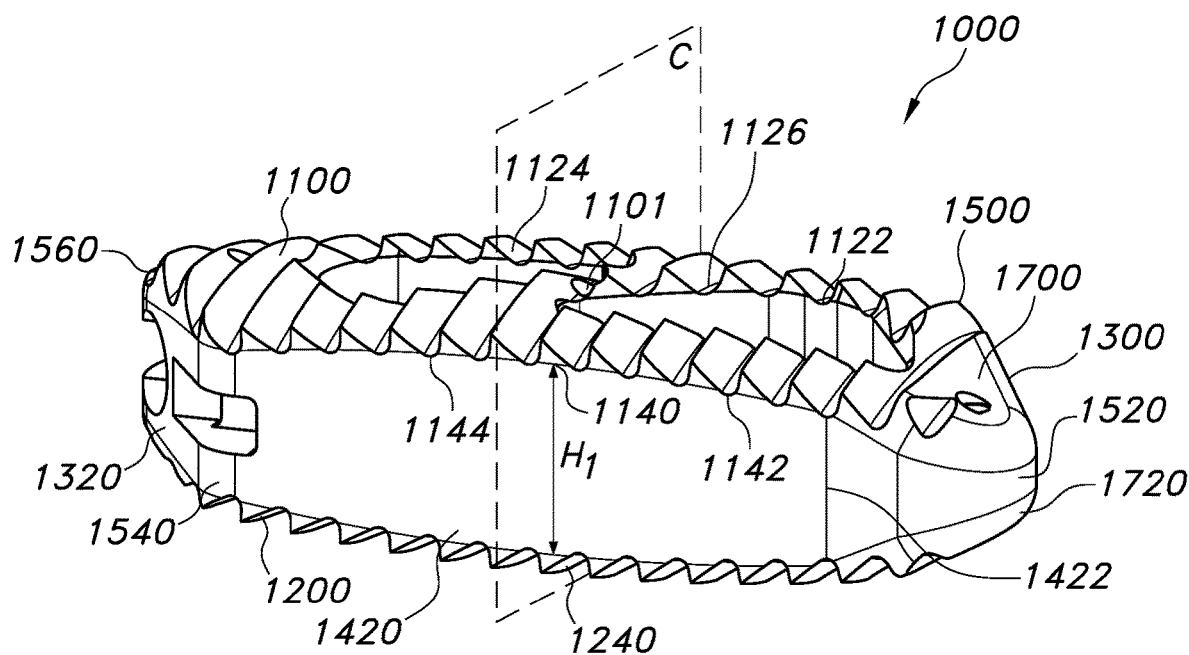

The outermost point 1101 of the superior convex surface 1100 is the apex of the implant. The length of an imaginary horizontal line connecting the outermost point 1101 to the outermost point 1201 of the inferior convex surface 1200 corresponds with the apex height of the implant, with a height H1. Referring now to FIGS. 1E-1G, the apex and the four vertical edges 1500, 1422, 1540, 1560 of the bi-convex implant differ in height from one another. This provides for the asymmetric design of the implant along the median M and coronal C planes.

The anterior lateral vertical edge 1500 is the highest with height H12. The vertical anterior medial edge 1422 has height H14 that is shorter than H12. The posterior medial vertical edge 1540 has a height H16 that is shorter than H14, and the posterior lateral vertical edge 1560 has a height H18 that is shorter than H16. The anterior medial vertical tip 1520 has a height H14' that is shorter than H18. In other words, the heights of the edges of the implant are interrelated in the following order of progressively shorter heights: H1>H12>H14>H16>H18>H14'.

Typically, the implant heights range from 5 mm to 25 mm. In preferred embodiments, the implant heights range from 9 mm to 18 mm.

a. Sagittal Profile of the Bi-Convex Implant

Referring now to FIGS. 1A-1C, 1F-1H, the bi-convex implant has an apex along its coronal plane C. The lower-most points of the superior convex surface 1100 along the coronal plane C, and the upper-most points of the inferior convex surface 1200 along the coronal plane C, are the lower-most lateral point 1120, the lower-most medial point 1140, the upper-most lateral point 1220 and the upper-most medial point 1240.

From the outermost point 1101, the superior convex surface 1100 connects with the superior end of the anterior lateral vertical edge 1500 in a curved manner, in the form of a curved line 1122. Similarly, the outermost point 1101 of the superior convex surface 1100 connects with the superior end of the posterior lateral vertical edge 1560 in a curved manner, in the form of a curved line 1124. The outermost point 1101 of the superior convex surface 1100 connects with the superior end of the vertical anterior medial edge 1422 in a curved manner, in the form of a curved line 1142. Similarly, the outermost point 1101 of the superior convex surface 1100 connects with the superior end of the posterior medial vertical edge 1540 in a curved manner, in the form of a curved line 1144. Similarly, the outermost point 1101 of the superior convex surface 1100 connects with the superior end of the anterior medial vertical tip 1520 in a curved manner, in the form of a curved line 1142.

Similar geometry connects the inferior convex surface 1200 with the four outer edges of the implant. From the outermost point 1201 of the inferior convex surface 1200 connects with the inferior end of the anterior lateral vertical edge 1500 in a curved manner, in the form of a curved line 1222 (not shown). Similarly, the outermost point 1201 of the inferior convex surface 1200 connects with the inferior end of the posterior lateral vertical edge 1560 in a curved manner, in the form of a curved line 1224 (not shown). The outermost point 1201 of the inferior convex surface 1200 connects with the inferior end of the vertical anterior medial edge 1422 in a curved manner, in the form of a curved line 1242 (not shown). Similarly, the outermost point 1201 of the inferior convex surface 1200 connects with the inferior end of the posterior medial vertical edge 1540 in a curved manner, in the form of a curved line 1244 (not shown). Similarly, the outermost point 1201 of the inferior convex surface 1200 connects with the inferior end of the anterior medial vertical tip 1520 in a curved manner, in the form of a curved line 1242 (not shown).

The curvatures are defined by the differences between the apex height H1 and edge heights H12, H14, H16, and H18. These height differences are designated as $a_1$, $a_2$, $a_3$, and $a_4$. The distance of each of the edges from the coronal plane C as measured by a straight line that runs from each edge and intersects at a right angle with the coronal plane C is designated as $b_1$, $b_2$, $b_3$, and $b_4$. The distance of each of the edges from the outermost point 1101 of the superior convex surface 1100 or the outermost point 1201 of the inferior convex surface 1200 is designated as $b_{1S}$, $b_{2S}$, $b_{3S}$, and $b_{4S}$. The different values for a and b elements define the sagittal profile of the implants. The elements $a_2$, $a_3$, $a_4$, $b_1$, $b_2$, $b_3$, $b_4$, $b_{1S}$, $b_{2S}$, $b_{3S}$, and $b_{4S}$ are shown in FIGS. 1A and 1B.

The curvatures of the curved lines 1122, 1124, 1142, 1144, 1222, 1224, 1242, and 1244 may be calculated using Equation 1 (above). Preferred values for a and b are presented in Table 3.

b. Coronal Profile of the Bi-Convex Implant

Referring now to FIGS. 1C and 1F, the outermost point 1101 of the superior convex surface 1100 connects with the lower-most lateral point 1120 in a curved manner, in the form of a curved line 1126. Also, the outermost point 1101 of the superior convex surface 1100 connects with the lower-most medial point 1140 in a curved manner, in the form of a curved line 1128. Similarly, the outermost point 1201 of the inferior convex surface 1200 connects with the lower-most lateral point 1220 in a curved manner, in the form of a curved line 1226 (not shown). Also, the outermost point 1201 of the inferior convex surface 1200 connects with the lower-most medial point 1240 in a curved manner, in the form of a curved line 1228 (not shown).

The curvatures of the curved lines 1126, 1128, 1226 (not shown), and 1228 (not shown) may be calculated using Equation 1. Preferred values for a and values for the width of the implant that can be used to derive the values for b are listed in Table 3. Each of the curved lines may have its own curvature, which may be calculated using different values for a and b, designated as $a_5$ and $a_6$, and $b_5$ and $b_6$. The different values for $a_5$ and $a_6$ and $b_5$ and $b_6$ elements define the coronal profile of the implants, and are shown in FIG. 1C.

The curvatures of the superior convex surface 1100 and inferior convex surface 1200 are configured to match the concave surfaces of the endplates of the vertebra when the implant is inserted at a posterior oblique insertion angle. Thus, following the initial insertion step, the implant is not rotated. Rather, it is inserted at the angle that corresponds with an ultimate placement between the vertebral bodies.

As shown in the Figures, the lateral longitudinal surface 1400 and the medial longitudinal surface 1420 are flat. However, these surfaces could have any desired three-dimensional geometry (e.g. curved surface) that does not interfere with implantation and performance of the implant.

ii. Angles

Figure 1I:
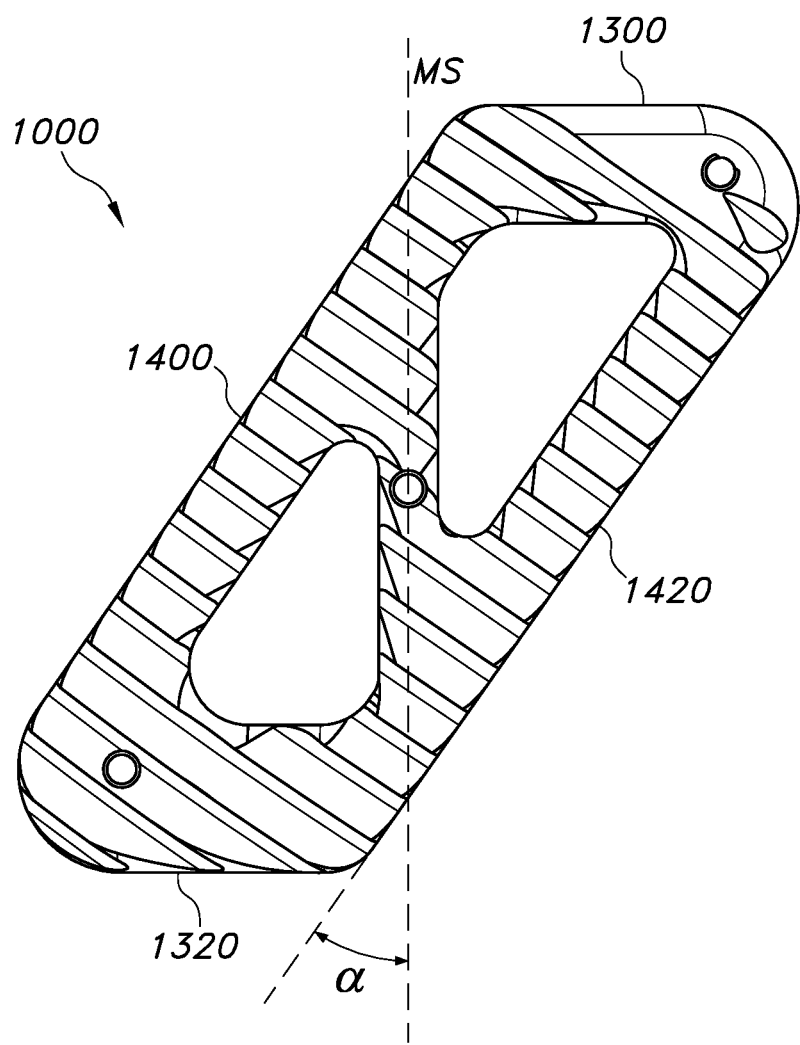

FIG. 1I shows a top view of the implant. The anterior vertical surface 1300 is parallel to the posterior vertical surface 1320, and the lateral longitudinal surface 1400 is parallel to the medial longitudinal surface 1420.

The bi-convex implants are configured to be inserted into a patient's spine at an oblique insertion angle α relative to the medial axis of the spine MS. In a preferred embodiment, the insertion angle α ranges from 30° to 40°, preferably approximately 35°, relative to the medial axis of the spine MS. Once inserted, the posterior vertical surface 1320 and the anterior vertical surface 1300 are at about a 90° angle relative to the medial axis of the spine MS, and the oblique divider 1620 is generally aligned with the medial axis of the spine MS. In other embodiments, the insertion angle α ranges from 20° and 50°.

Figure 7:
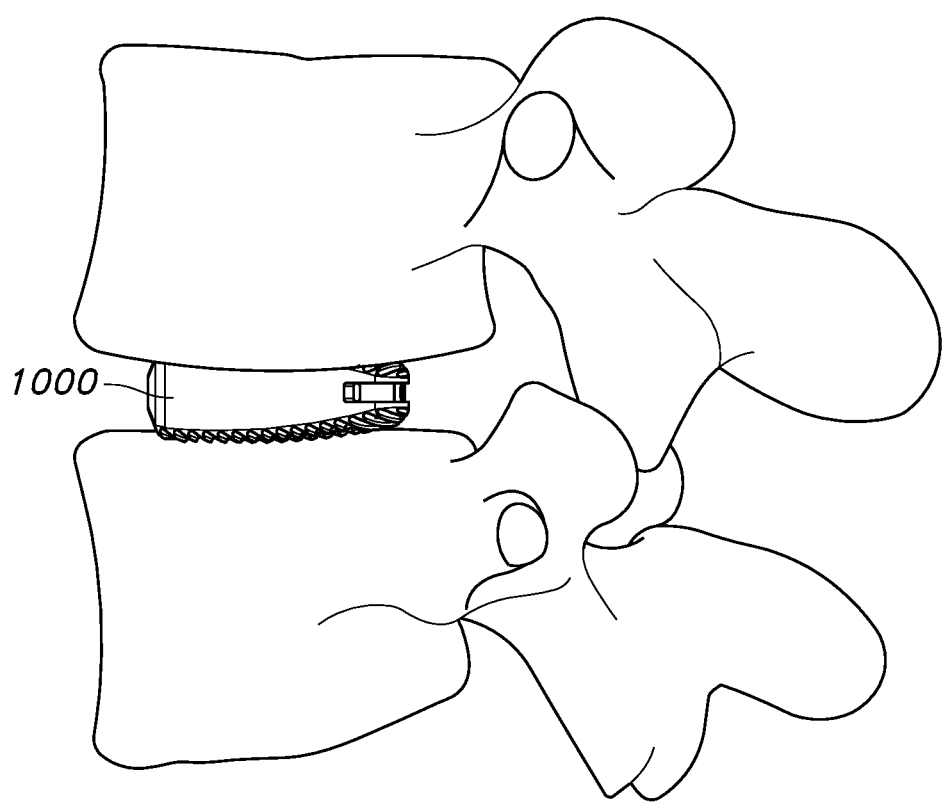
FIG. 7 is a lateral view of a spine with an intervertebral spinal fusion implant positioned between two adjacent vertebrae.

An illustration of a lateral view of bi-convex implant following insertion between two adjacent vertebral bodies is provided in FIG. 7. Optionally, supplemental fixation systems (not shown in Figure), such as one or more polyaxial bone screws and/or one or more pedicle screws, optionally with one or more rods, are used with the implant to achieve the desired spacing between the vertebral bodies.

iii. Lengths and Widths

The implant length L can be measured along its medial axis M with a line from the anterior medial vertical tip 1520 to posterior lateral vertical edge 1560, as shown in FIG. 1D. In preferred embodiments, the bi-convex implant length L ranges from 30 mm to 45 mm. For example, suitable implant lengths L include, but are not limited to, 34 mm, 39 mm, and 41 mm.

The bi-convex implant width W can be measured along its coronal axis C with a horizontal line from the medial longitudinal surface 1420 to the lateral longitudinal surface 1400, as shown in FIG. 1D. In preferred embodiments, the implant width W ranges from 9 mm to 18 mm.

Implants of various lengths and edge heights are contemplated. Dimensions for a preferred bi-convex implant are listed in Table 3. Dimensions for the sagittal and coronal profiles of a superior convex surface are shown. Dimensions for the sagittal and coronal profiles of an inferior convex surface can be the same in this preferred bi-convex implant.

Implant length L and the heights H1, H12, H14, H16, H18, and H14' are interrelated. A change in any one of these dimensions will change the others. For example, elongation of a particular implant that increases implant length L will result in an implant having the same H1, but different H12, H14, H16, H18, and H14'. This will also change the curvatures of the curved lines 1122, 1124, 1142, 1144, 1222, 1224, 1242, and 1244.

TABLE 3

Dimensions (mm) of a preferred bi-convex implant.

| | |
|---|---|
| Widths | 10 mm and 12 mm |
| Lengths | 34 mm, 39 mm and 41 mm |
| Heights | 9 mm through 18 mm |
| Sagittal Profile | $a_1$: 0.03 mm to 0.08 mm |
| | $a_2$: 0.08 mm to 0.14 mm |
| | $a_3$: 0.09 mm to 0.13 mm |
| | $a_4$: 0.11 mm to 0.15 mm |
| | $b_1$: 12 mm to 16 mm |
| | $b_2$: 11.5 mm to 15.5 mm |
| | $b_3$: 12 mm to 16.1 mm |
| | $b_4$: 17 mm to 21 mm |
| | $b_{1S}$: 13.4 mm to 16.8 mm |
| | $b_{2S}$: 12.7 mm to 17 mm |
| | $b_{3S}$: 13.4 mm to 16.8 mm |
| | $b_{4S}$: 17 mm to 20.6 mm |
| Coronal Profile | $a_5$: 0.5 mm to 0.88 mm |
| | $a_6$: 0.5 mm to 0.88 mm |
| | $b_5$: 5 mm to 6 mm |
| | $b_6$: 5 mm to 6 mm | iv. Surfaces

The superior convex surface 1100 and the inferior convex surface 1200 of the bi-convex implant typically contain a plurality of bone engagement members 1160, such as ridges or teeth, as shown in FIG. 1F. In some embodiments, the engagement members 1160 partially cover these surfaces, or are present only on one of the two surfaces.

Generally, the posterior vertical surface 1320 includes an instrument portion 1322 for insertion of an instrument, such as an insertion or implantation tool, with inner threads 1324 for mating with outer threads. The posterior lateral vertical edge 1560 has an indented cut 1326 and the posterior medial vertical edge 1540 has an indented cut 1328. The cuts 1326 and 1328 are designed to receive elements of an insertion or implantation tool to further secure the implant on the handle.

v. Markers

In preferred embodiments, one or more radiopaque markers, such as tantalum rods, can be positioned in the bi-convex implant, such as at the anterior and posterior ends of the bi-convex implant. One or more markers may be positioned at one or more locations in the implant. For example, as shown in FIG. 1F, a marker 1170 may be positioned at the anterior medial vertical tip 1520, while another marker 1180 is positioned at the posterior lateral vertical edge 1560. In other embodiments, a marker 1190 may also be positioned in the center of oblique divider 1620, as is shown in FIG. 1F.

B. Offset Bi-Convex Implant

1. Heights and Shape

Figure 2B:
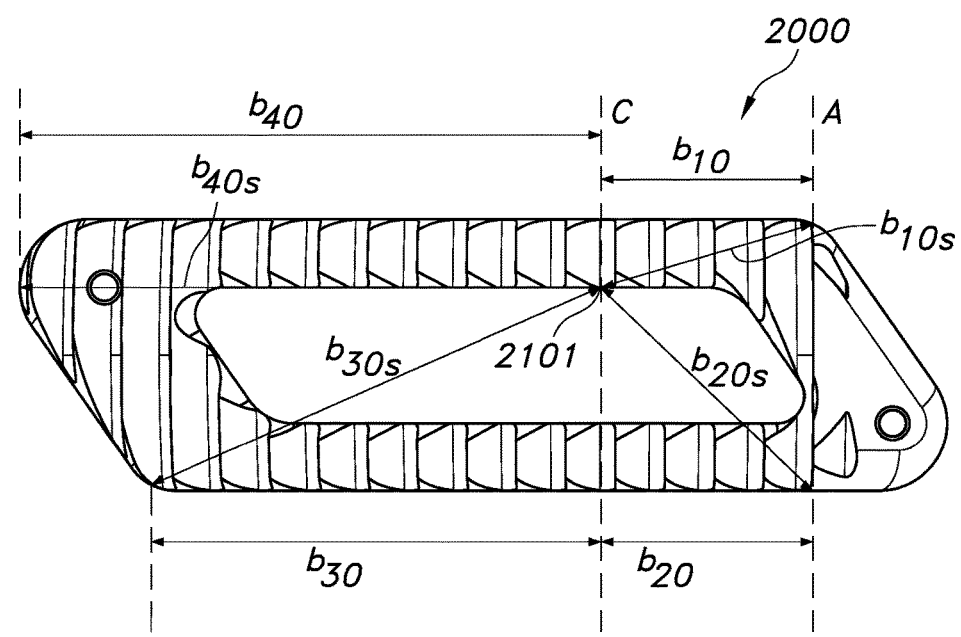

In another embodiment, the implant is an offset bi-convex implant. These implants are asymmetric along the median M and coronal C planes, and are symmetric along the transverse T plane, as shown in FIGS. 2E and 2F.

FIGS. 2A-2J depict the general shape of a typical offset bi-convex implant.

The offset bi-convex implant 2000 is formed of a superior convex surface 2100, an inferior convex surface 2200, an anterior vertical surface 2300, a posterior vertical surface 2320, a lateral longitudinal surface 2400, a medial longitudinal surface 2420, and a central opening 2600.

The anterior vertical surface 2300 meets with the lateral longitudinal surface 2400 and the medial longitudinal surface 2420 forming the anterior lateral vertical edge 2500 and anterior medial vertical tip 2520, respectively. Similarly, the posterior vertical surface 2320 meets with lateral longitudinal surface 2400 and the medial longitudinal surface 2420 forming the posterior lateral vertical edge 2560 and posterior medial vertical edge 2540, respectively. Each of the vertical edges 2500, 2422, 2540, and 2560 has a superior end and an inferior end that contact the superior convex surface 2100 and the inferior convex surface 2200, respectively. In preferred embodiments, the edges 2500, 2540, and 2560 are curved. As shown on the figures, the anterior lateral vertical edge 2500, anterior medial vertical tip 2520, posterior medial vertical edge 2540, and posterior lateral vertical edge 2560 generally correspond with the ends of the lateral and medial longitudinal surfaces, while vertical anterior medical edge 2422 is an imaginary line located along the medial longitudinal surface 2420 towards the anterior end.

At the anterior end of the implant, the anterior lateral vertical edge 2500 is connected with the medial longitudinal surface 2420 along an anterior coronal plane A perpendicular to the medial longitudinal surface 2420. The anterior coronal plane A intersects the medial longitudinal surface 2420 along a vertical anterior medial line 2422. The vertical anterior medial edge 2422 has a superior end contacting the superior convex surface 2100 and an inferior end contacting the inferior convex surface 2200. The anterior coronal plane A intersects the superior convex surface 2100 along an superior horizontal line 2130, and the inferior convex surface 2200 along an inferior horizontal line 2260 (not shown). From the superior horizontal line 2130, the superior convex surface 2100 tapers downwards and forms the superior oblique surface 2700. From the inferior horizontal line 2260 (not shown), the inferior convex surface 2200 tapers upwards and forms the inferior oblique surface 2720.

i. Heights of Implant Elements

The outermost point 2101 of the superior convex surface 2100 is the apex of the implant. An imaginary horizontal line connecting the outermost point 2101 to the outermost point 2201 of the inferior convex surface 2200 forms the apex height of the implant, with a height H2. Referring now to FIGS. 2E-2H, the four vertical edges 2500, 2422, 2540, 2560 of the offset bi-convex implant differ in height H from one another. This provides for the asymmetric design of the implant along the median M and coronal C planes.

The anterior lateral vertical edge 2500 is the highest with height H22. The vertical anterior medial edge 2422 has height H24 that is shorter than H22. The posterior medial vertical edge 2540 has a height H26 that is shorter than H24, and the posterior lateral vertical edge 2560 has a height H28 that is shorter than H26. The anterior medial vertical tip 2520 has a height H24' that is shorter than H28. In other words, the heights of edges of the implant are interrelated in the following order of progressively shorter heights: H2>H22>H24>H26>H28>H24'.

Typical implant heights range from 5 mm to 25 mm. In preferred embodiments, the implant heights range from 9 mm to 18 mm.

a. Sagittal Profile of the Offset Bi-Convex Shape

As shown in FIGS. 2A-2B, 2D-2I, the offset bi-convex implant has an apex along its anterior coronal plane C positioned anteriorly from the middle of the implant. The lower-most points of the superior convex surface 2100 and the upper-most points of the inferior convex surface 2200 along the coronal plane C are the lower-most lateral point 2120, the lower-most medial point 2140, the upper-most lateral point 2220 and the upper-most medial point 2240.

From the outermost point 2101, the superior convex surface 2100 connects with the superior end of the anterior lateral vertical edge 2500 in a curved manner, in the form of a curved line 2122. Similarly, the outermost point 2101 of the superior convex surface 2100 connects with the superior end of the posterior lateral vertical edge 2560 in a curved manner, in the form of a curved line 2124. The outermost point 2101 of the superior convex surface 2100 connects with the superior end of the vertical anterior medial edge 2422 in a curved manner, in the form of a curved line 2142. Similarly, the outermost point 2101 of the superior convex surface 2100 connects with the superior end of the posterior medial vertical edge 2540 in a curved manner, in the form of a curved line 2144.

Similar geometry connects the inferior convex surface 2200 with the four outer edges of the implant. From the outermost point 2201, the inferior convex surface 2200 connects with the inferior end of the anterior lateral vertical edge 2500 in a curved manner, in the form of a curved line 2222 (not shown). Similarly, the outermost point 2201 of the inferior convex surface 2200 connects with the inferior end of the posterior lateral vertical edge 2560 in a curved manner, in the form of a curved line 2224 (not shown). The outermost point 2201 of the inferior convex surface 2200 connects with the inferior end of the vertical anterior medial edge 2422 in a curved manner, in the form of a curved line 2242 (not shown). Similarly, the outermost point 2201 of the inferior convex surface 2200 connects with the inferior end of the posterior medial vertical edge 2540 in a curved manner, in the form of a curved line 2244 (not shown).

At the apex, the implant has the greatest height H2. The curvatures of the curved lines 2122, 2124, 2142, 2144, 2222 (not shown), 2224 (not shown), 2242 (not shown), and 2244 (not shown) may be calculated using Equation 1 above. Preferred values for a and b are presented in Table 4.

The curvatures of the curved lines are defined by the differences between the apex height H2 and edge heights H22, H24, H26 and H28. These height differences are designated as $a_{10}$, $a_{20}$, $a_{30}$ and $a_{40}$. The distances of the anterior lateral vertical edge 2500, anterior medial vertical tip 2520, vertical anterior medial edge 2422, posterior lateral vertical edge 2560 and the posterior medial vertical edge 2540 from the coronal plane C are designated as $b_{10}$, $b_{20}$, $b_{30}$, $b_{40}$, $b_{10S}$, $b_{20S}$, $b_{30S}$ and $b_{40S}$, respectively, which can be determined from the length of the implants, as shown in FIG. 2B. The distance of each of the edges from the coronal plane C as measured by a straight line that runs from each edge and intersects at a right angle with the coronal plane C is designated as $b_{10}$, $b_{20}$, $b_{30}$, and $b_{40}$. The distance of each of the edges from the outermost point 2101 of the superior convex surface 2100 or the outermost point 2201 of the inferior convex surface 2200 is designated as $b_{10S}$, $b_{20S}$, $b_{30S}$, and $b_{40S}$. Preferred values for $b_{10}$, $b_{20}$, $b_{30}$, $b_{40}$, $b_{10S}$, $b_{20S}$, $b_{30S}$ and $b_{40S}$ are presented in Table 4. The elements $a_{10}$, $a_{20}$, $a_{30}$ and $a_{40}$ and $b_{10}$, $b_{20}$, $b_{30}$, $b_{40}$, $b_{10S}$, $b_{20S}$, $b_{30S}$ and $b_{40S}$ are labeled in FIGS. 2A, 2B and 2D.

b. Coronal Profile of the Offset Bi-Convex Implants

Figure 2C:
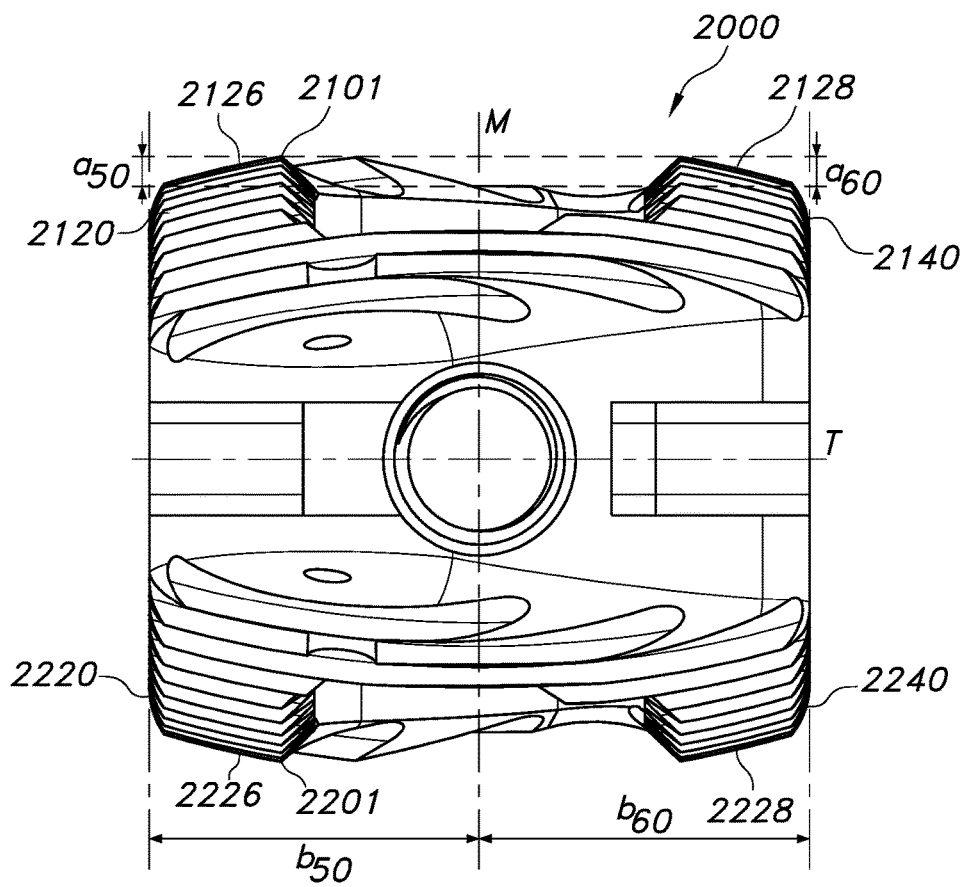
Figure 2D:
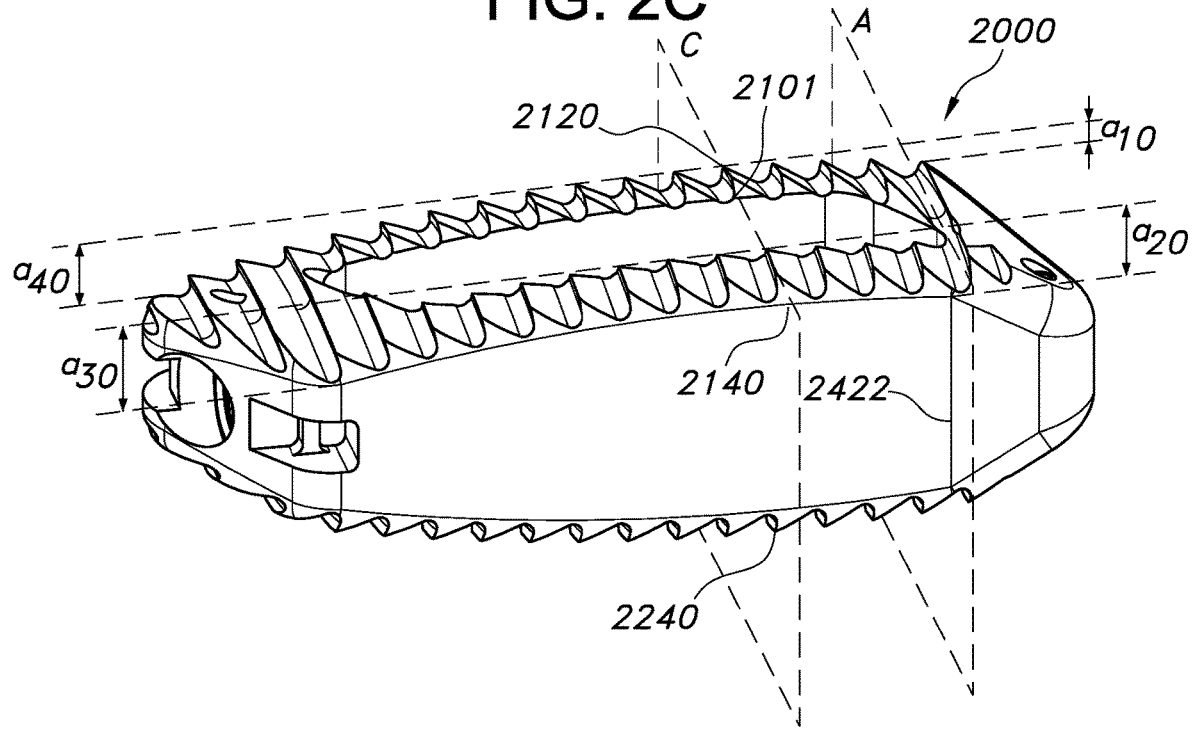
Figure 2E:
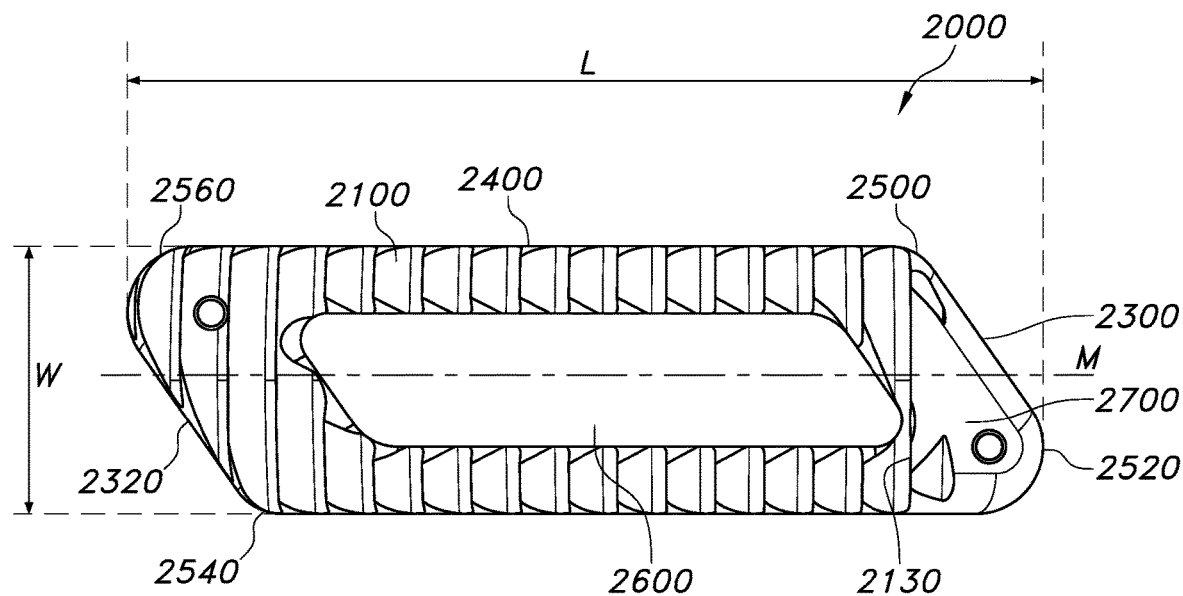
Figure 2F:
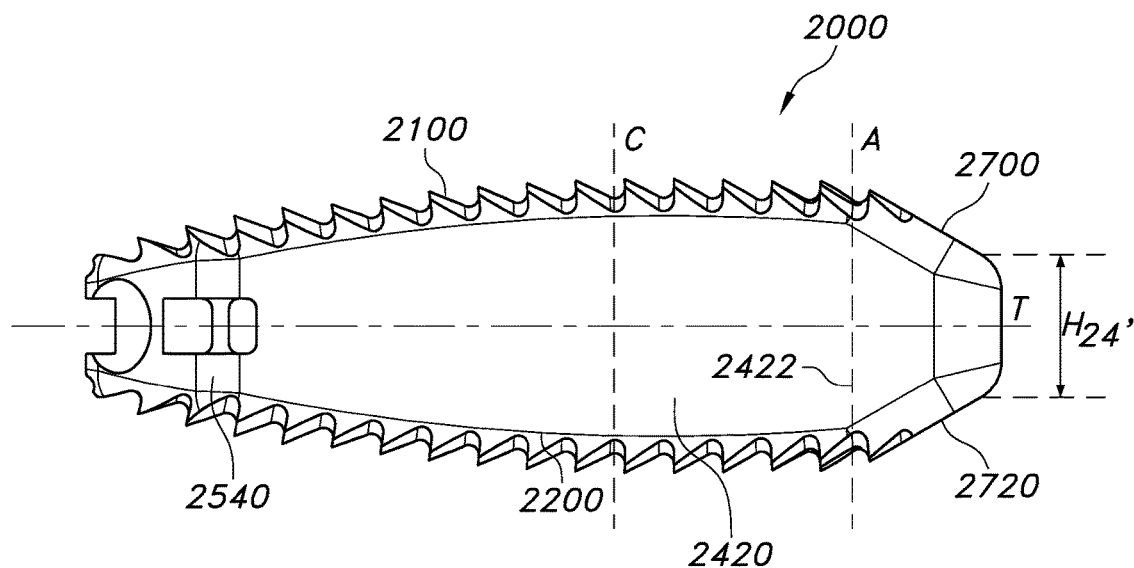

Referring now to FIG. 2C, the outermost point 2101 of the superior convex surface 2100 connects with the lower-most lateral point 2120 in a curved manner, in the form of a curved line 2126. Also, the outermost point 2101 of the superior convex surface 2100 connects with the lower-most medial point 2140 in a curved manner, in the form of a curved line 2128. Similarly, the outermost point 2201 of the inferior convex surface 2200 connects with the upper-most lateral point 2220 in a curved manner, in the form of a curved line 2226. Also, the outermost point 2201 of the inferior convex surface 2200 connects with the upper-most medial point 2240 in a curved manner, in the form of a curved line 2228.

The curvatures of the curved lines 2126, 2128, 2226, and 2228 may be calculated using Equation 1 (above).

In preferred embodiments, each of the curved lines has its own curvature represented by dimensions a and b. For example, the superior convex surface of the offset bi-convex implant may have different values for a, designated as $a_{10}$, $a_{20}$, $a_{30}$ and $a_{40}$, and different values for b, designated as $b_{10}$, $b_{20}$, $b_{30}$, $b_{40}$, $b_{10S}$, $b_{20S}$, $b_{30S}$, and $b_{40S}$. Each of the $a_{10}$, $a_{20}$, $a_{30}$ and $a_{40}$ values may range from 1.6 mm to 4.2 mm, and each of the $b_{10}$, $b_{20}$, $b_{30}$, $b_{40}$, $b_{10S}$, $b_{20S}$, $b_{30S}$, and $b_{40S}$ may range from 7.2 mm to 28.3 mm, along the sagittal plane. In some embodiments, the dimensions $b_{10}$, $b_{20}$, $b_{30}$, $b_{40}$, $b_{10S}$, $b_{20S}$, $b_{30S}$, and $b_{40S}$ have equal values. In other embodiments, the dimensions $b_{10}$, $b_{20}$, $b_{30}$, $b_{40}$, $b_{10S}$, $b_{20S}$, $b_{30S}$, and $b_{40S}$ have different values.

The same implant may have two other values for a, $a_{50}$ and $a_{60}$, and two other values for b, $b_{50}$ and $b_{60}$, along the coronal plane (C). The $a_{50}$ and $a_{60}$ values may each range from 0.5 mm to 1.1 mm, and each of the $b_{50}$ and $b_{60}$ values may range from 5 mm to 6 mm. In some embodiments, the dimensions $b_{50}$ and $b_{60}$ have equal values. The inferior convex surface has the same or similar values for a and b.

Preferred values for a and b are presented in Table 4. Each of the lines may have its own curvature, which may be calculated using different values for a, designated as $a_{50}$ and $a_{60}$, and b, designated as $b_{50}$ and $b_{60}$. The different values for the dimensions $a_{50}$, $a_{60}$, $b_{50}$ and $b_{60}$ define the coronal profile of the implants. Elements $a_{50}$, $a_{60}$, $b_{50}$, and $b_{60}$ d are labeled in FIG. 2C, and preferred values are presented in Table 4.

Collectively, the curved lines form the offset bi-convex shape of the implant, and are configured to match the concave surfaces of the endplates of the vertebra when the implant is inserted at a posterior oblique insertion angle.

As shown in the figures, the lateral longitudinal surface 2400 and the medial longitudinal surface 2420 are flat. However, these surfaces could have any desired three-dimensional geometry that does not interfere with implantation and performance of the implant.

ii. Angles

Figure 2G:
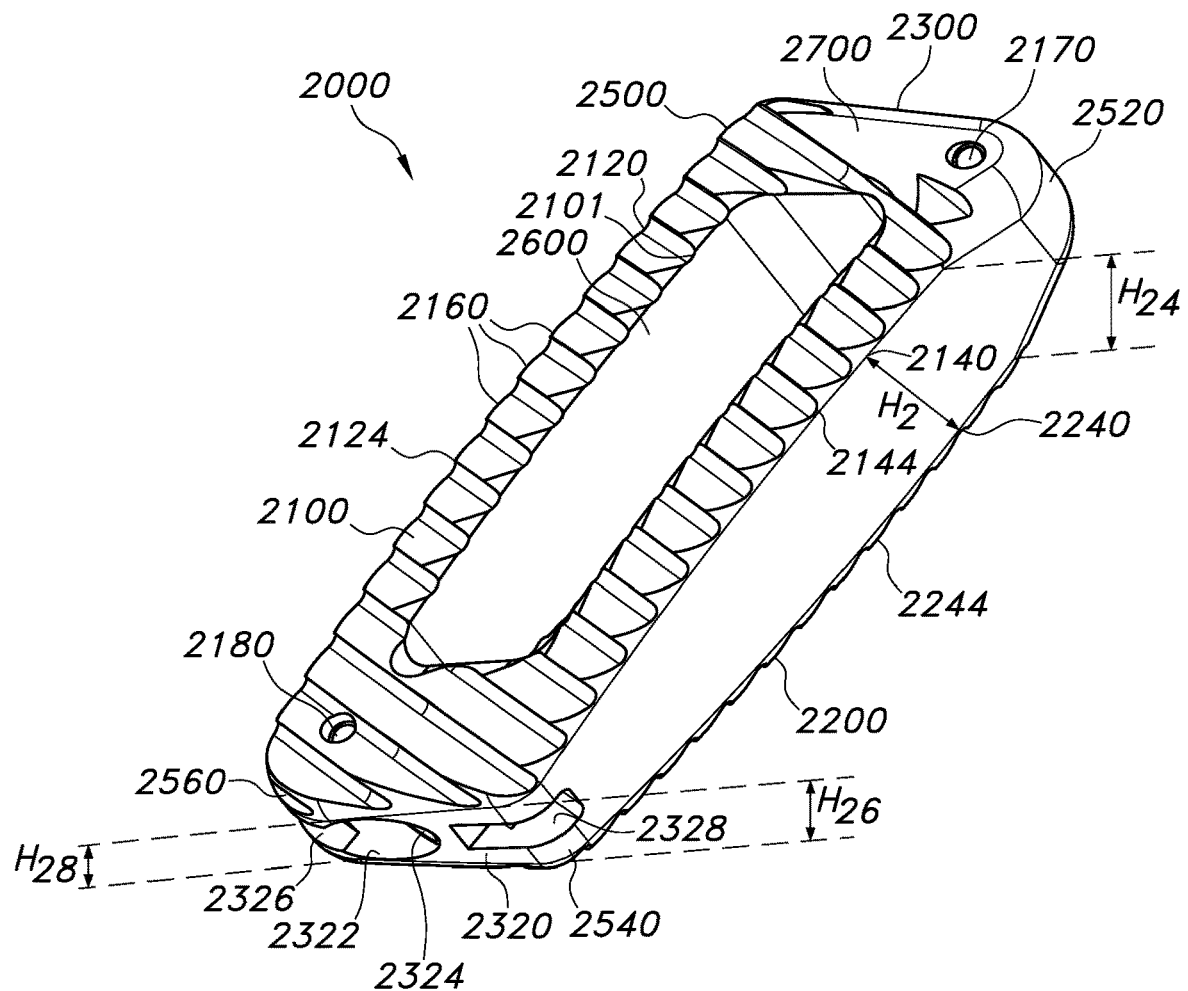
Figure 2H:
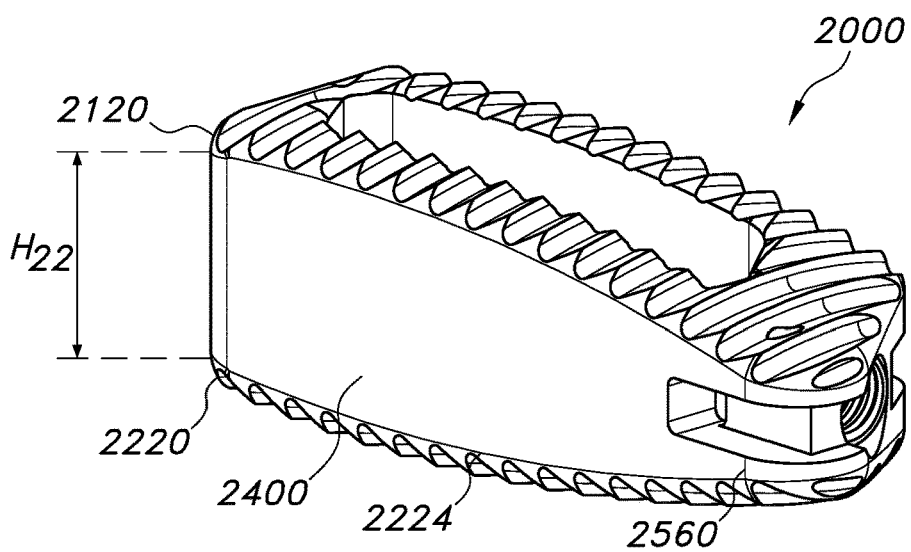
Figure 2I:
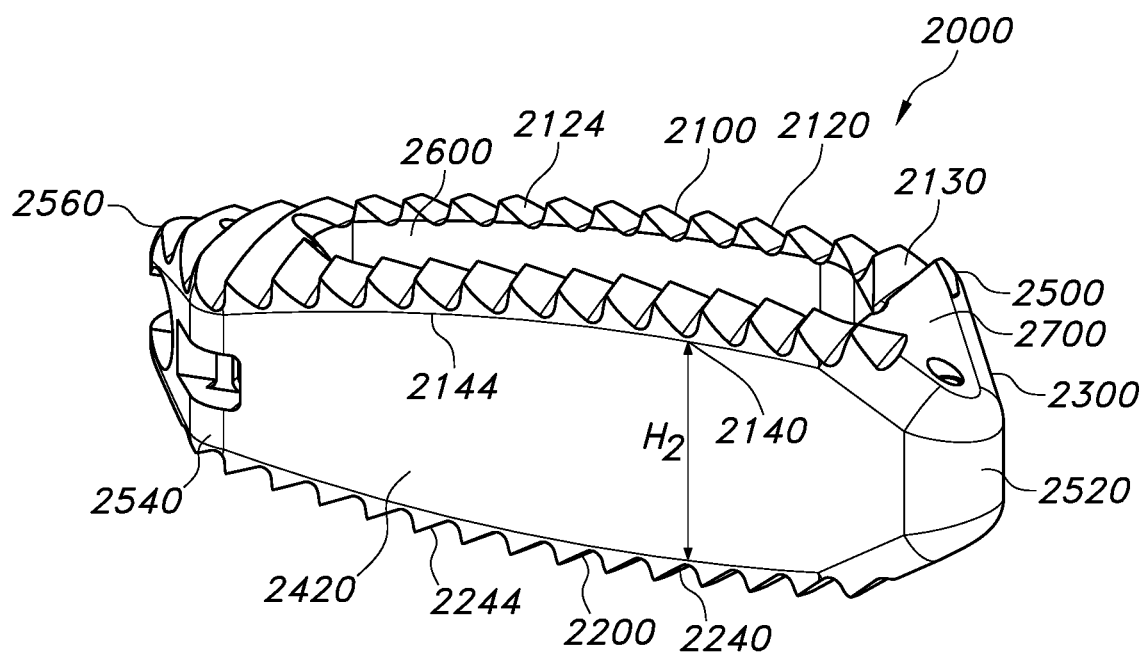
Figure 2J:
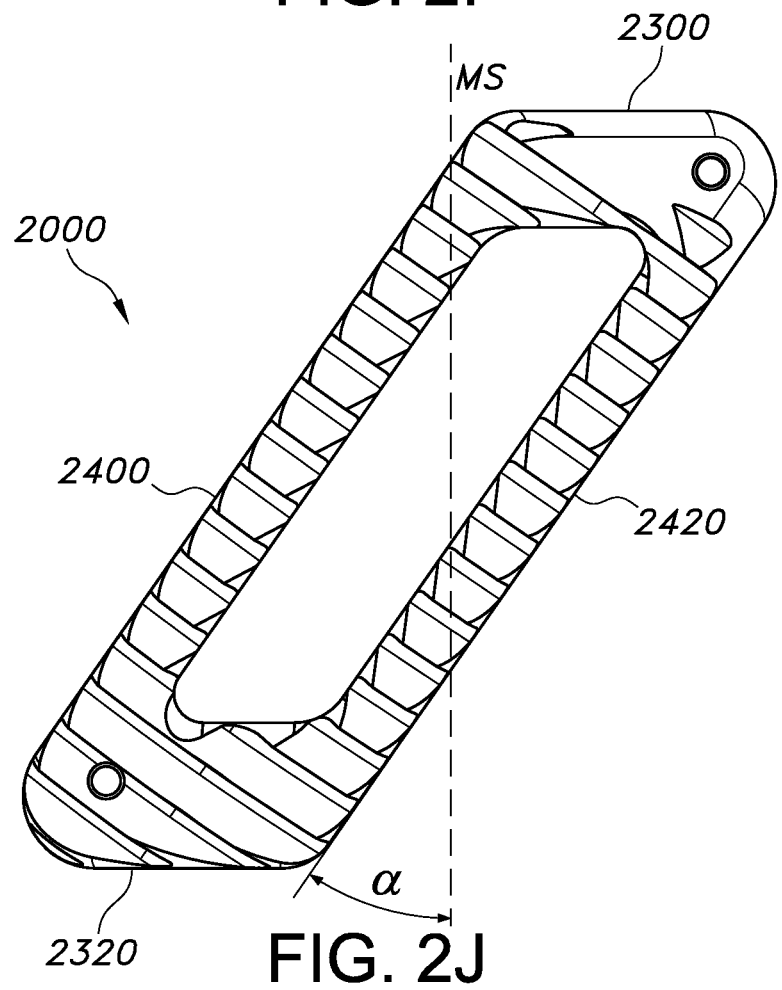

FIG. 2J shows a top view of the implant and demonstrates that the anterior vertical surface 2300 is parallel to the posterior vertical surface 2320, and the lateral longitudinal surface 2400 is parallel to the medial longitudinal surface 2420.

In all embodiments, the offset bi-convex implants are designed for an oblique insertion angle α. In a preferred embodiment, the insertion angle α ranges from 30° to 40° relative to the medial axis of the spine MS. Once inserted, the posterior vertical surface 2320 and the anterior vertical surface 2300 are at about a 90° angle to the medial axis of the spine MS, and the medial longitudinal surface 2420 is positioned at about 35° relative to the medial axis of the spine MS. In other embodiments, the insertion angle α ranges from 20° and 50°.

iii. Lengths and Widths

The implant length L can be measured along its medial axis M with a straight line from the anterior medial vertical tip 2520 to posterior lateral vertical edge 2560, as shown in FIG. 2E. In preferred embodiments, the offset bi-convex implant length L ranges from 30 mm to 45 mm. For example, suitable implant lengths L include, but are not limited to, 34 mm, 39 mm, and 41 mm.

The offset bi-convex implant width W can be measured along its coronal axis A with a horizontal line from the medial longitudinal surface 2420 to the lateral longitudinal surface 2400, as shown in FIG. 2E. In preferred embodiments, the implant width W ranges from 10 mm to 12 mm.

Implants of various lengths and/or widths are contemplated. Implants with lengths and/or widths within the range of plus/minus 50% of the preferred implant length L and implant width W are contemplated.

Preferred dimensions for the offset bi-convex implant are presented in Table 4. Dimensions for the sagittal and coronal profiles of a superior convex surface are shown. Dimensions for the sagittal and coronal profiles of an inferior convex surface can be the same in this preferred offset bi-convex implant.

TABLE 4

Dimensions (mm) of a preferred offset bi-convex implant.

| | |
|---|---|
| Widths | 10 mm and 12 mm |
| Lengths | 34 mm, 39 mm and 41 mm |
| Heights | 9 mm through 18 mm |
| Sagittal Profile | $a_{10}$: 1.6 mm to 1.8 mm |
| | $a_{20}$: 1.6 mm to 1.7 mm |
| | $a_{30}$: 3.7 mm to 4.1 mm |
| | $a_{40}$: 3.8 mm to 4.2 mm |
| | $b_{10}$: 7.2 mm to 14.2 mm |
| | $b_{20}$: 7.2 mm to 14.2 mm |
| | $b_{30}$: 16.2 mm to 23.2 mm |
| | $b_{40}$: 21.3 mm to 28.3 mm |
| | $b_{10S}$: 7.8 mm to 14.8 mm |
| | $b_{20S}$: 11.5 mm to 18.5 mm |
| | $b_{30S}$: 18.5 mm to 25.5 mm |
| | $b_{40S}$: 21 mm to 28 mm |
| Coronal Profile | $a_{50}$: 0.5 mm to 0.85 mm |
| | $a_{60}$: 0.55 mm to 1.1 mm |
| | $b_{50}$: 5 mm to 6 mm |
| | $b_{60}$: 5 mm to 6 mm | iv. Surfaces

The superior convex surface 2100 and the inferior convex surface 2200 of the offset bi-convex implant contain bone engagement members 2160, such as ridges or teeth, as shown in FIG. 2G. In some embodiments, the engagement members 2160 partially cover these surfaces, or are present only on one of the two surfaces.

The posterior vertical surface 2320 has an instrument portion 2322 with inner threads 2324 for mating with outer threads of an instrument, such as an insertion or implantation tool. The posterior lateral vertical edge 2560 has an indented cut 2326 and the posterior medial vertical edge 2540 has an indented cut 2328. The cuts 2326 and 2328 are configured to receive a portion of an insertion or implantation tool to further secure the implant on the handle.

v. Markers

In preferred embodiments, one or more radiopaque markers, such as tantalum rods, can be positioned in the offset bi-convex implant, such as at the anterior and posterior ends of the offset bi-convex implant. Referring now to FIG. 2G, a marker 2170 is positioned at the anterior medial vertical edge 2520, while another marker 2180 is positioned at the posterior lateral vertical edge 2560. In other embodiments, multiple markers may be positioned at any of these or other locations in the implant.

EXAMPLE

Example 1. Correction of Lordotic Angle in Patients Using Implants Described Above Three patients with lumbar pathology received the offset bi-convex implant. They were operated on to restore the natural lumbar lordosis and disc heights. The offset bi-convex implants were positioned in between two adjacent vertebrae at the site of pathology according to the method described above. Patient 1 had a pre-operative lordotic angle measurement from L4-S1 of 11°, which was corrected and measured 16° following the operation. Patients 2 and 3 had operative lordotic angle measurements from L4-L5 of 5°, which were corrected and measured 7° following the operation.

Unless defined otherwise, all technical and scientific terms used herein have the same meanings as commonly understood by one of skill in the art to which the disclosed subject matter belongs.

We claim:

1. A unitary intervertebral fusion implant for spinal fusion between two adjacent vertebrae comprising
   a superior convex surface,
   an inferior convex surface, and
   four vertical edges, wherein each edge has a different height than the other edges, wherein each edge comprises a superior end and an inferior end, wherein each superior end terminates at the superior convex surface, and wherein each inferior end terminates at the inferior convex surface,
   wherein the superior convex surface comprises a first outermost point, the first outermost point being the apex of the implant, and
   wherein the inferior convex surface comprises a second outermost point, wherein the apex is the highest point of the implant, and wherein none of the four vertical edges contains the apex, and
   wherein the implant is configured for a transforaminal or posterior approach at an oblique insertion angle.

2. The intervertebral fusion implant of claim 1, wherein the first outermost point and the second outermost point are positioned on a median plane of the implant, and the implant has a bi-convex shape.

3. The intervertebral fusion implant of claim 1, wherein the first outermost point and the second outermost point are positioned offset from a median plane of the implant, and the implant has an offset bi-convex shape.

4. The intervertebral fusion implant of claim 1, wherein the height of an imaginary line connecting the apex and the second outermost point is the apex height, and wherein the apex height is greater than each of the heights of the four vertical edges.

5. The intervertebral fusion implant of claim 1, wherein the implant further comprises an opening for receiving a bone graft material.

6. The intervertebral fusion implant of claim 1, wherein the superior convex surface and inferior convex surface further comprise one or more bone engagement members.

7. The intervertebral fusion implant of claim 1, wherein curvatures of the inferior and superior convex surfaces match the concavities of the two adjacent vertebrae at an insertion angle when the insertion angle is an oblique angle relative to the median plane of the spine.

8. The intervertebral fusion implant of claim 1, wherein a curvature of the superior convex surface is defined by connecting the first outermost point to each of the superior ends of each of the four vertical edges to form four superior curved lines of different curvatures, and
   wherein a curvature of the inferior convex surface is defined by connecting the second outermost point to each of the inferior ends of each of the four edges to form four inferior curved lines of different curvatures.

9. The intervertebral fusion implant of claim 8, wherein the curvature of each of the superior curved lines or the inferior curved lines is calculated using Equation 1:

$$E = \frac{\sqrt{b^2 - a^2}}{b} \quad \text{Eq. 1}$$

wherein
E is eccentricity of the curved line;
a is the difference between the apex height and the height of the edge connected with the first or second outermost point via the curved line, and
b is the length of a straight line running from the edge to the first outermost point or the second outermost point.

10. The intervertebral fusion implant of claim 9, wherein a ranges from 0.03 mm to 0.88 mm and b ranges from 5 mm to 21 mm, and wherein the implant has a bi-convex shape.

11. The intervertebral fusion implant of claim 9, wherein a ranges from 0.5 mm to 4.2 mm and b ranges from 5 mm to 28.3 mm, and wherein the implant has an offset bi-convex shape.

12. The intervertebral fusion implant of claim 2, further comprising a central opening and an oblique divider, and wherein the apex is located on the oblique divider.

13. The intervertebral fusion implant of claim 1, wherein
(a) the first outermost point of the superior convex surface is positioned on a median plane of the implant,
(b) the second outermost point of the inferior convex surface is positioned on a median plane of the implant, and
wherein the implant further comprises:
(c) an anterior vertical surface and a posterior vertical surface,
(d) a lateral longitudinal surface and a medial longitudinal surface,
(e) a central opening, and
(f) an oblique divider dividing the central opening,
wherein the distance between the first outermost point and the second outermost point is the apex height, and
wherein the apex height is greater than each of the heights of the four vertical edges, and
wherein the implant has a bi-convex shape.

14. The intervertebral fusion implant of claim 13, wherein a first curvature of the superior convex surface and a second curvature of the inferior convex surface along a sagittal plane of the implant form a sagittal profile of the implant, and
wherein the first curvature is defined by connecting the first outermost point with each of the superior ends of the four vertical edges to form four superior curved lines, and wherein the second curvature is defined by connecting the second outermost point with each of the inferior ends of the four vertical edges to form four inferior curved lines,
wherein the curvature of each of the superior curved lines or the inferior curved lines is calculated from Equation 1:

$$E = \frac{\sqrt{b^2 - a^2}}{b} \quad \text{Eq. 1}$$

wherein
E is eccentricity of the curved line;
a is the difference between the apex height and the height of the edge connected with the first or second outermost point via the curved line, and
b is the length of a straight line running from the edge to a coronal plane passing through the first and second outermost points and meeting the coronal plane at a right angle.

15. The intervertebral fusion implant of claim 13, wherein a first curvature of the superior convex surface and a second curvature of the inferior convex surface along a coronal plane of the implant form a coronal profile of the implant, and
wherein the first curvature is defined by connecting the first outermost point with a lower-most lateral point and a lower-most medial point to form two superior curved lines, and wherein the second curvature is defined by connecting the second outermost point with an upper-most lateral point and an upper-most medial point to form two inferior curved lines,
wherein the curvature of each of the superior curved lines or the inferior curved lines is calculated from Equation 1:

$$E = \frac{\sqrt{b^2 - a^2}}{b} \quad \text{Eq. 1}$$

wherein
E is eccentricity of the curved line;
a is the difference between the apex height and the height of the lower-most lateral point, the lower-most medial point, the upper-most lateral point, or the upper-most medial point connected with the first or second outermost point via the curved line, and
b is the length of a straight line running from the lower-most lateral point, the lower-most medial point, the upper-most lateral point, or the upper-most medial point to a median plane passing through the first and second outermost points and meeting the median plane at a right angle.

16. The intervertebral fusion implant of claim 14, wherein a ranges from 0.03 mm to 0.15 mm and b ranges from 11.5 mm to 21 mm.

17. The intervertebral fusion implant of claim 15, wherein a ranges from 0.5 mm to 0.88 mm and b ranges from 5 mm to 6 mm.

18. The intervertebral fusion implant of claim 1, wherein
(a) the first outermost point of the superior convex surface is positioned offset from a median plane of the implant,
(b) the second outermost point of the inferior convex surface is positioned offset from a median plane of the implant, and
wherein the implant further comprises:
(c) an anterior vertical surface and a posterior vertical surface,
(d) a lateral longitudinal surface and a medial longitudinal surface, and
(e) a central opening,
wherein the distance between the first outermost point and the second outermost point is the apex height, and
wherein the apex height is greater than each of the heights of the four vertical edges, and
wherein the implant has an offset bi-convex shape.

19. The intervertebral fusion implant of claim 18, wherein a first curvature of the superior convex surface and a second curvature of the inferior convex surface along a sagittal plane of the implant form a sagittal profile of the implant, and wherein the first curvature is defined by connecting the first outermost point with each of the superior ends of the four vertical edges to form four superior curved lines, and wherein the second curvature is defined by connecting the second outermost point with each of the inferior ends of the four vertical edges to form four inferior curved lines, wherein the curvature of each of the superior curved lines or the inferior curved lines is calculated from Equation 1:

$$E = \frac{\sqrt{b^2 - a^2}}{b} \quad \text{Eq. 1}$$

wherein
- E is eccentricity of the curved line;
- a is the difference between the apex height and the height of the edge connected with the first or second outermost point via the curved line, and
- b is the length of a straight line running from the superior ends or the inferior ends of the vertical edges to a coronal plane passing through the first and second outermost points and meeting the coronal plane at a right angle.

20. The intervertebral fusion implant of claim 18, wherein a first curvature of the superior convex surface and a second curvature of the inferior convex surface along a coronal plane of the implant form a coronal profile of the implant, and wherein the first curvature is defined by connecting the first outermost point with a lower-most lateral point and a lower-most medial point to form two superior curved lines, and wherein the second curvature is defined by connecting the second outermost point with an upper-most lateral point and an upper-most medial point to form two inferior curved lines, wherein the curvature of each of the superior curved lines or the inferior curved lines is calculated from Equation 1:

$$E = \frac{\sqrt{b^2 - a^2}}{b} \quad \text{Eq. 1}$$

wherein
- E is eccentricity of the curved line;
- a is the difference between the apex height and the height of the lower-most lateral point, the lower-most medial point, the upper-most lateral point, or the upper-most medial point connected with the first or second outermost point via the curved line, and
- b is the length of a straight line running from the lower-most lateral point, the lower-most medial point, the upper-most lateral point, or the upper-most medial point to the median plane and meeting the median plane at a right angle.

21. The intervertebral fusion implant of claim 19, wherein a ranges from 1.6 mm to 4.2 mm and b ranges from 7.2 mm to 28.3 mm.

22. The intervertebral fusion implant of claim 20, wherein a ranges from 0.5 mm to 1.1 mm and b ranges from 5 mm to 6 mm.

23. A spinal fusion method for increasing or decreasing a lordotic angle comprising inserting a unitary intervertebral fusion implant between two adjacent vertebrae in a patient in need of a spinal fusion via a transforaminal or posterior approach at an oblique insertion angle, the implant comprising
- a superior convex surface,
- an inferior convex surface, and
- four vertical edges, wherein each edge has a different height than the other edges, wherein each edge comprises a superior end and an inferior end, wherein each superior end terminates at the superior convex surface, and wherein each inferior end terminates at the inferior convex surface, wherein the superior convex surface comprises a first outermost point, the first outermost point being the apex of the implant, and wherein the inferior convex surface comprises a second outermost point, wherein the apex is the highest point of the implant, and wherein none of the four vertical edges contains the apex.

24. The method of claim 23, wherein the oblique insertion angle ranges from 30° to 40° relative to a medial axis of a spine.

25. The method of claim 23, further comprising
attaching to one or more of the vertebrae one or more supplemental fixation systems, and
adjusting the supplemental fixation system to increase or decrease the lordotic angle.

* * * * *